United States Patent
Gygi et al.

(10) Patent No.: US 8,669,116 B2
(45) Date of Patent: Mar. 11, 2014

(54) DETECTION AND QUANTIFICATION OF MODIFIED PROTEINS

(75) Inventors: Steven P. Gygi, Foxboro, MA (US); Junmin Peng, Atlanta, GA (US)

(73) Assignee: President and Fellows of Harvard College, Cambridge, MA (US)

( * ) Notice: Subject to any disclaimer, the term of this patent is extended or adjusted under 35 U.S.C. 154(b) by 1314 days.

(21) Appl. No.: 10/506,877

(22) PCT Filed: Mar. 11, 2003

(86) PCT No.: PCT/US03/07527
§ 371 (c)(1), (2), (4) Date: Jul. 29, 2005

(87) PCT Pub. No.: WO03/078962
PCT Pub. Date: Sep. 25, 2003

(65) Prior Publication Data
US 2006/0148093 A1  Jul. 6, 2006

Related U.S. Application Data

(60) Provisional application No. 60/363,179, filed on Mar. 11, 2002.

(51) Int. Cl.
*C12Q 1/37* (2006.01)
*C07K 1/22* (2006.01)
*G01N 33/68* (2006.01)

(52) U.S. Cl.
CPC ........ *G01N 33/6848* (2013.01); *G01N 33/6842* (2013.01); *C12Q 1/37* (2013.01); *G01N 2440/36* (2013.01); *G01N 2560/00* (2013.01); *C07K 1/22* (2013.01)
USPC ................ 436/173; 435/23; 435/24; 530/413

(58) Field of Classification Search
None
See application file for complete search history.

(56) References Cited

U.S. PATENT DOCUMENTS 6,391,649 B1 * 5/2002 Chait et al. ............... 436/173
6,465,199 B1   10/2002 Craig et al. ............... 435/7.4

(Continued)

FOREIGN PATENT DOCUMENTS

WO   WO 03/102172 A1   12/2003   .............. C12N 9/00

OTHER PUBLICATIONS

Wang et al. "Antibacterial peptides in stimulated human granulocytes Characterization of ubiquitinated histone H1A" Eur J Biochem. Jan. 2002;269(2):512-8.*

(Continued)

*Primary Examiner* — Christine Foster
(74) *Attorney, Agent, or Firm* — Sonia K. Guterman; Sanjeev K. Mahanta; Anna E. Stanford

(57) ABSTRACT

The invention provides a method detecting and quantifying proteins by mass spectrophotometric analysis using peptide internal standards and provides a highly sensitive way of detecting protein modifications. In one aspect, the invention provides a method for determining a site of ubiquitination in a polypeptide and for evaluating ubiquitination targets in a population of polypeptides. In this way, a proteome ubiquitination map can be obtained which comprises information relating to the ubiquitination states of a plurality of cellular polypeptides. Maps can be obtained for a variety of different types of cells and cell states. For example, ubiquitination targets in normal and diseased cells can be evaluated. Preferably, the map is stored as data files in a database. Individual ubiquitinated polypeptides identified can be used to generate molecular probes diagnostic of a cell state and/or can serve as targets for agents that modulate one or more cellular processes.

20 Claims, 13 Drawing Sheets

Ubiquitinated protein

Signature peptide:
• 114-Da tag on K*
• Miscleavage of K*

(56) References Cited

U.S. PATENT DOCUMENTS

| | | | |
|---|---|---|---|
| 7,183,116 B2 | 2/2007 | Aebersold et al. | 436/86 |
| 7,198,896 B2 * | 4/2007 | Rush et al. | 435/7.23 |
| 2002/0087273 A1 | 7/2002 | Anderson et al. | 702/19 |
| 2005/0287608 A1 | 12/2005 | Madura et al. | 435/7.9 |

OTHER PUBLICATIONS

Marotti et al. "Direct identification of a G protein ubiquitination site by mass spectrometry" Biochemistry vol. 41(16):5067-74, Published on Web Feb. 27, 2002.*

Laub et al. "Modulation of calmodulin function by ubiquitin-calmodulin ligase and identification of the responsible ubiquitylation site in vertebrate calmodulin" (1998) Eur. J. Biochem. 255: 422-431.*

Ling et al. "Histidine-Tagged Ubiquitin Substitutes for Wild-Type Ubiquitin in *Saccharomyces cerevisiae* and Facilitates Isolation and Identification of in Vivo Substrates of the Ubiquitin Pathway" J Analytical Biochemistry 282, 54-64 (2000).*

Figueiredo-Pereira et al. "Accumulation of ubiquitinated proteins in mouse neuronal cells induced by oxidative stress" Mol Biol Rep. Mar. 1997;24(1-2):35-8.*

Yang et al. "Ubiquitin Protein Ligase Activity of IAPs and Their Degradation in Proteasomes in Response to Apoptotic Stimuli" Science May 5, 2000:vol. 288. No. 5467, pp. 874-877.*

Peng et al. "A proteomics approach to understanding protein ubiquitination" Nature biotechnology, (Aug. 2003) vol. 21, No. 8, pp. 921-926.*

Warren et al. "Electrospray ionization tandem mass spectrometry of model peptides reveals diagnostic fragment ions for protein ubiquitination" Rapid Commun. Mass Spectrom. 2005; 19: 429-437).*

Rodriguez et al. ("Multiple C-Terminal Lysine Residues Target p53 for Ubiquitin-Proteasome-Mediated Degradation" Mol Cell Biol. Nov. 2000; 20(22): 8458-8467).*

Denis et al. "Tryptic digestion of ubiquitin standards reveals an improved strategy for identifying ubiquitinated proteins by mass spectrometry" Proteomics. Mar. 2007;7(6):868-74.

Bast et al. "Translational Crossroads for Biomarkers" Clin Cancer Res 2005; 11(17), 6103-6108.

LaBaer et al. "So, You Want to Look for Biomarkers" Journal of Proteome Research 2005; 4, 1053-1059.

Baker "In Biomarkers We Trust?" Nature Biotechnology 2005; 23(3), 297-304.

"Inhibition of the 26S Proteasome by Polyubiquitin Chains Synthesized to Have Defined Lengths", Piotrowski et al., Publication, Jun. 2, 1997, pp. 23712-23721.

* cited by examiner

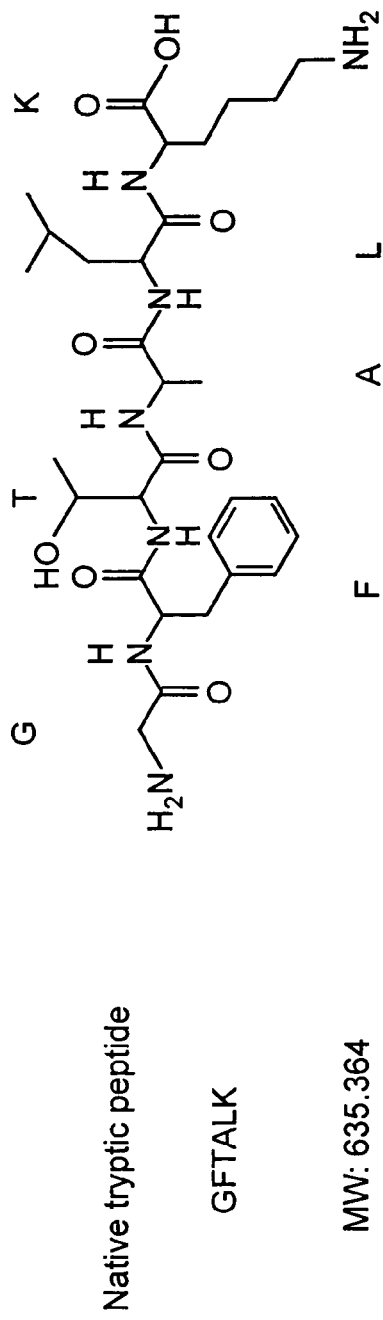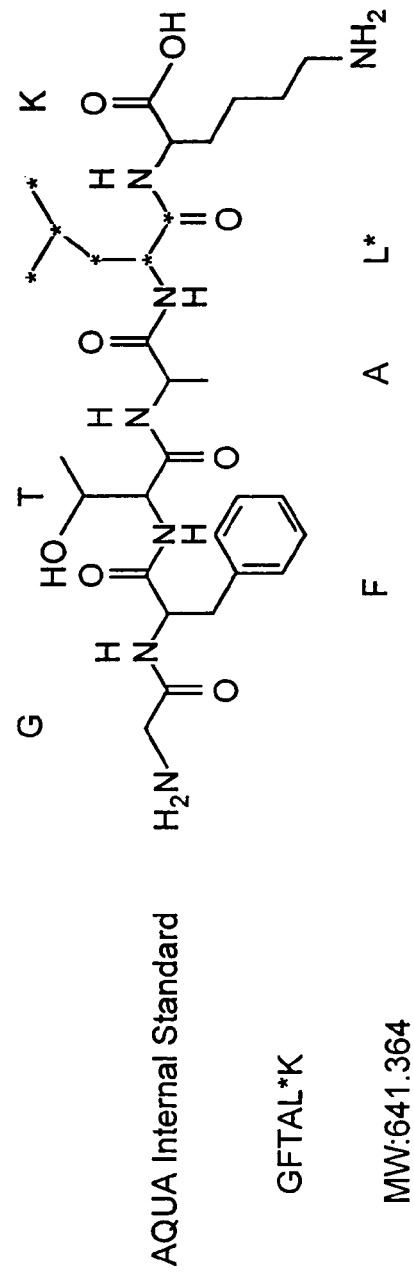
FIG. 5A
Native tryptic peptide
GFTALK
MW: 635.364
AQUA Internal Standard
GFTAL*K
MW: 641.364
* = stable isotope (e.g. $^{13}C$)

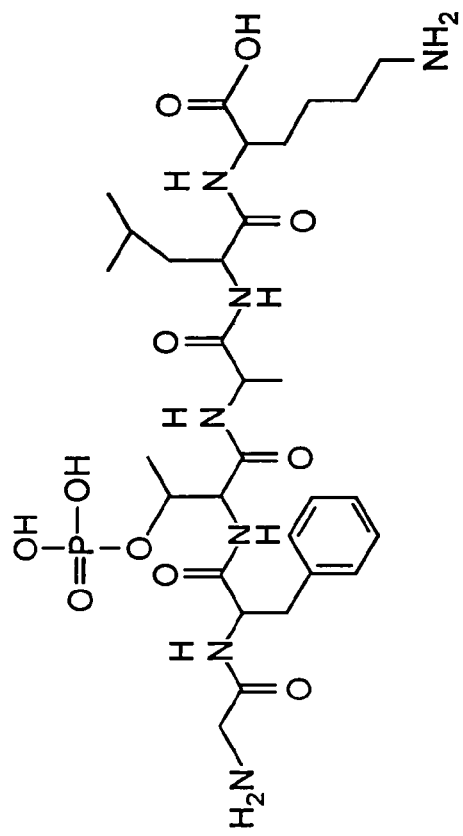
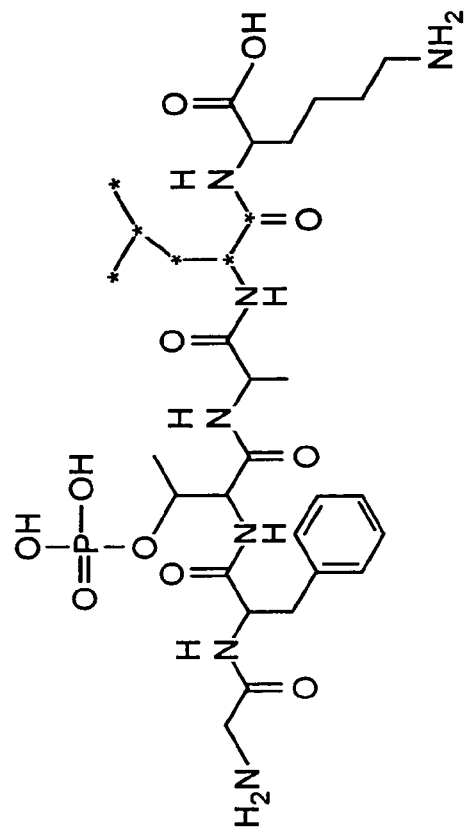
Native phosphopeptide
GF(pT)ALK
MW: 715.754
AQUA phosphopeptide Internal Standard
GF(pT)AL*K
MW: 721.75
* = stable isotope (e.g. $^{13}C$)
FIG. 5B

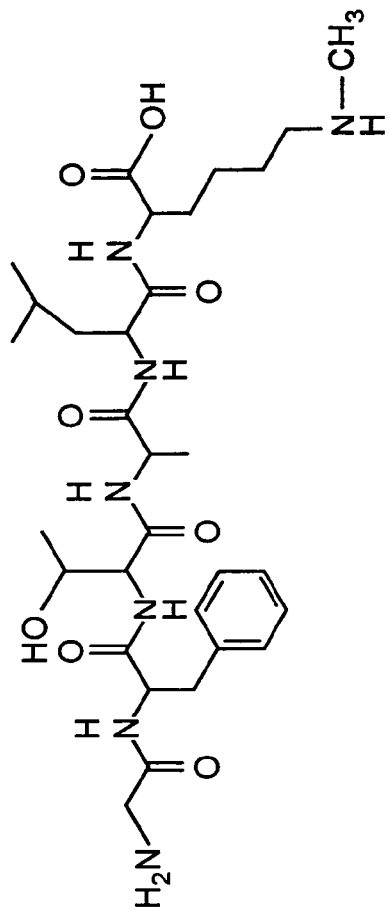
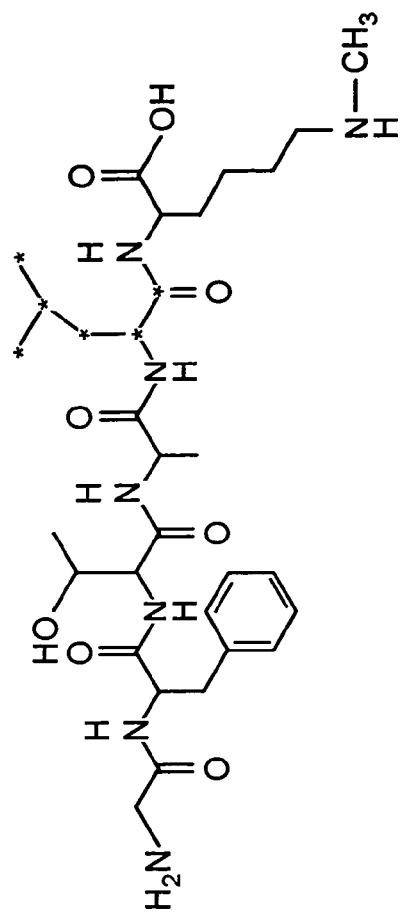
Native methylated peptide
GFTAL(mK)
MW: 649.79
AQUA methylated peptide
Internal Standard
GFTAL*(mK)
MW:655.79
* = stable isotope (e.g. $^{13}C$)
FIG. 5C

| Name | #sites |
|---|---|
| Ubiquitin | 5 |
| ECM21 | 5 |
| SAM2 | 4 |
| YHRD97C | 3 |
| HXT7 | 3 |
| GNP1 | 3 |
| YILD41W | 2 |
| YHLD1DC | 2 |
| LSB1 | 2 |
| ZEO1 | 2 |
| PHOM | 2 |
| URA3 | 2 |
| GDH1 | 2 |
| ERG5 | 2 |
| ERG3 | 2 |
| YGR26DC | 2 |
| YMR295C | 2 |

```
MPFITSRPVA KNSSHSLSET DLNQSKGQPF QPSPTKKLGS MQQRRRSSTI RHALSSLLGG
ANVHSPAVLN NTTKGGNNNG NIRSSNIDAQ LLGKKQNKCP PNARRHSTT AIQGSISDSA
TTTPRSSTSD TNRRTSGRLS VDQEPRISGG RYSQIEEDST VLDFDDDHNS SAVVSSDLSS
TSLTRLANSK KFNEQFLIEY LTARGLLGPK TVLSNEYLKI SISTSGESVF LPTISSNDDE
YLSRLNGLND GTDDAEADFF MDGIDQQEGN TPSLATTAAA TESGGSINEN RDTLLRENNS
GDHPGSGSEL NTRSVEIDSS MVSYSIAVIV SVKKPTRFTD MQLELCSRVK VFVNTGVPPT
KTFNEEFYNA ASMKVNLNDE NFDLFVPLSI SPDGQMIENN SNDRQVRLFK NIPTEERLYL
DKTKTKASLL NAIDVNKTHL YQPGDYVFLV PVVFSNHIPE TIYLPSARVS YRLRLATKAI
NRKGFYRQDS NSPQPIVSPD SSSSLSSTTS SLKLTETESA QAHRRISNTL FSKVKNHLHM
SSHQLKNEES GEEDIFAEYP IKVIRTPPPV AVSTANKPIY INRVWTDSLS YEISFAQKYV
SLNSEVPIKI KLAPICKNVC VKRIHVSITE RVTFVSKGYE YEYDQITPVA KDPYNPYYLD
FASKRRKERS VSLFEIRTKE KGTRALREEI VENSFNINLE SYSPFDDDSD SKGNPKERLG
ITEPIIIETK LKFPKYEDLD KRTAKIIPPY GIDAYTSIPN PEHAVANGPS HRRPSVIGFE
SGHKGSKSHE ENEKPVYDPK FHQDIIKSNS GLPVKTHTRL NIPKRGLYLD SLHFSNVYCR
HKLEIMIRIS KPDPECPSKL RHYEVLIDTP IFLVSEQGNS GNMELPTYDM ATMEGKGNQV
PLSMNSDFFG NICPPPPTFE EAISVPASPI VSPMGSPNIM ASYDPDLLSI QQLNLSRTTS
VSGPSGYSDD AGVPNVNRNS ISNANAMNGS ISNSAFVSGN SGQGVARARA TSVNDRSRFN
NLDKLLSTPS PVNRSHNSSP TNGLSQANGT VRIPNATTEN SKDKQNEFFK KGYTLANVKD
DEEQEGIVSS SSADSLLSHG NEPPRYDEIV PLMSDEE
```

FIG. 10A

| Site in Ub (K) | Signature peptide | SCX fraction | | Abundance |
|---|---|---|---|---|
| 48 | LIFAGK*QLEDGR | 48-56 | (9) | high |
| 63 | TLSDYNIQK*ESTLHLVLR | 65-72 | (8) | high |
| 11 | TLTGK*TITLEVESSDTIDNVK | 38-42 | (5) | medium |
| 27 | TITLEVESSDTIDNVK*SK | 41 | (1) | low |
| 6 | LISEEDLGMQIFVK*TLTGK | 38 | (1) | low |

FIG. 10B

| Name | Phosphopeptide sequence | Description of function |
|---|---|---|
| ACC1 | AVS*VSDLSYVANSQSSPLR | Acetyl.CoA carboxylase |
| CCC1 | GSGGTSELGGSEST*PLLR | Protein potentially in calcium regulation |
| CHO1 | DENDGYAS*DEVGGTLSR | Phosphatidylserine synthase |
| CHS1 | DDEYDDLNT*IDK | Chitin synthase I |
| CHS3 | NPSTLLPTS*SMFWNK | Chitin synthase III |
| ECM21 | NEES*GEEDIFAEYPIK | Protein possibly in cell wall biosynthesis |
|  | HALSS*LLGGANVHSPAVLNNTTK |  |
|  | RPS*VIGFLSGHK |  |
|  | S*HNSS*PTNGLSQANGTVR |  |
| GCD6 | EEIDS*EFEDEDFEK | Translation initiation factor eIF2B |
| HSP3D | ASGETAIHEPEPEAEQAVEDT*A | Heat shock protein located in cell membrane |
| LYP1 | LQVVSHET*DINEDEEEAHYEDK | High affinity lysine specific permease |
| MET4 | KYS*DNEDDEYDDADLHGFEK | Transcriptional activator |
| MYO3 | RGS*VYHVPLNPVQATAVR | Myosine type I |
| PHO84 | IHDT*S*DEDMAINGLER | Inorganic phosphate/H* symporter |
|  | NNDIESSS*PSQLQHEA |  |
| RAD16 | SVNYNELS*DDDTAVK | Nucleotide excision repair protein |
| Ubiquitin | TLS*DYNIQK | Protein for posttranslational modification |
| YDR119W | IEEINENS*PLLSAPSK | Member of major facilitator superfamily (MFS) |
| YDR348C | TNS*FDMPQLNTR | Protein of unknown function |
| YHR097C | ETVDDDSET*LNQLQDR | Protein of unknown function |
|  | LPSYEEAAGT*PK |  |
| YOR042W | KNPDEDEFLINS*DDEM | Protein of unknown function |
|  | SSGIDEDEVVT*PAEDAKEEEEEHPPLPAR |  |
|  | EQHHEDS*EEEDSWSQFVEK |  |
| YPL019C | HYIADLEDHES*S*DEEGTALPK | Vacuolar polyphosphate accumulation |

FIG. 10C

DETECTION AND QUANTIFICATION OF MODIFIED PROTEINS

RELATED APPLICATION

This application claims the benefit of the PCT/US03/07527 filed Mar. 11, 2003 which claims the benefit of the U.S. provisional application Ser. No. 60/363,179 filed Mar. 11, 2002, each of which is hereby incorporated herein in its entirety.

GOVERNMENT GRANTS

At least part of the work contained in this application was performed under government grant HG0041 from the National Institutes of Health, U.S. Department of Health and Human Services. The government may have certain rights in this invention.

FIELD OF THE INVENTION

This invention provides methods, reagents and kits for obtaining absolute quantification of proteins and their modifications directly from cell lysates. In particular, the invention provides peptide internal standards for use in high performance liquid chromatography (HPLC) with online detection by multistage mass spectrometry ($MS^n$). In one aspect, the invention also provided compositions, kits and methods for detective ubiquitination sites in proteins.

BACKGROUND OF THE INVENTION

There is a need to provide novel methods for the quantification of proteins and modified proteins from cell lysates. The current standard for protein detection (quantification) is based on immunoreactive detection (Western analysis). However, this technique requires the availability of an appropriately specific antibody. In addition, many antibodies only recognize proteins in an unfolded (denatured) form, cross-reactivity can be severely limiting, and quantification is generally relative.

The development of methods and instrumentation for automated, data-dependent electrospray ionization (ESI) tandem mass spectrometry (MS/MS) in conjunction with microcapillary liquid chromatography (LC) and database searching has significantly increased the sensitivity and speed of the identification of gel-separated proteins. Microcapillary LC-MS/MS has been used successfully for the large-scale identification of individual proteins directly from mixtures without gel electrophoretic separation (Link et al., 1999; Opitek et al., 1997). However, while these approaches dramatically accelerate protein identification, quantities of the analyzed proteins cannot be easily determined, and these methods have not been shown to substantially alleviate the dynamic range problem also encountered by the 2DE/MS/MS approach. Therefore, low abundance proteins in complex samples are also difficult to analyze by the microcapillary LC/MS/MS method without their prior enrichment.

There is thus a need to provide methods for the accurate comparison of protein expression levels between cells in two different states, particularly for comparison of low abundance proteins.

Another methodology has recently been described. ICAT™ reagent technology makes use of a class of chemical reagents called isotope coded affinity tags (ICAT). These reagents exist in isotopically heavy and light forms which are chemically identical with the exception of eight deuterium or hydrogen atoms, respectively. Proteins from two cells lysates can be labeled independently with one or the other ICAT reagent at cysteinyl residues. After mixing and proteolysing the lysates, the ICAT-labeled peptides are isolated by affinity to a biotin molecule incorporated into each ICAT reagent. ICAT-labeled peptides are analyzed by LC-MS/MS where they elute as heavy and light pairs of peptides. Quantification is performed by determining the relative expression ratio relating to the amount of each ICAT-labeled peptide pair in the sample.

Identification of each ICAT-labeled peptide is performed by a second stage of mass spectrometry (MS/MS) and sequence database searching. The end result is relative protein expression ratios on a large scale. The major drawback to this technique are 1) quantification is only relative; 2) specialized chemistry is required, and 3) database searches are hindered by the presence of the large ICAT reagent molecule, and 4) relative amounts of posttranslationally modified (e.g., phosphorylated) proteins are transparent to analysis.

SUMMARY

The present invention provides reagents, kits, and methods for accurate quantification of proteins and methods for using the same. In particular, the method is useful for detecting and quantitating modified proteins and identifying sites of protein modification, such as sites of ubiquitination. The reagents, kits, and methods of the invention are useful for rapid, high throughput analysis of proteomes.

The invention also provides a method for generating a peptide internal standard. The method comprises identifying a real or predicted peptide digestion product of a target polypeptide, determining the amino acid sequence of the peptide digestion product and synthesizing a peptide having the amino acid sequence. The peptide is labeled with a mass-altering label (e.g., by incorporating labeled amino acid residues during the synthesis process) and fragmented (e.g., by multi-stage mass spectrometry). Preferably, the label is a stable isotope. A peptide signature diagnostic of the peptide is determined, after one or more rounds of fragmenting, and the signature is used to identify the presence and/or quantity of a peptide of identical amino acid sequence in a sample.

Preferably, a labeled peptide is provided which co-elutes with an unlabeled peptide having the same amino acid sequence (i.e., a target peptide) in a chromatographic separation procedure (e.g., such as HPLC).

In one aspect, the mass-altering label is part of a peptide comprising a modification, and the peptide is fragmented to determine a peptide signature diagnostic of such a modified peptide. The modified residue in the peptide internal standard comprises a phosphorylated residue, a glycosylated residue, an acetylated residue, a ubiquitinated residue, a ribosylated residue, or a farnesylated residue, or another modification found in a cellular protein. In one aspect, panels of peptide internal standards are generated corresponding to (i.e., diagnostic of) different modified forms of the same protein.

Peptide internal standards corresponding to different peptide subsequences of a single target protein also can be generated to provide for redundant controls in a quantitative assay. In one aspect, different peptide internal standards corresponding to the same target protein are generated and differentially labeled (e.g., peptides are labeled at multiple sites to vary the amount of heavy label associated with a given peptide).

In another aspect, a panel of peptide internal standards corresponding to different amino acid subsequences of a single protein is used to scan for mutations in that protein. In a further aspect, peptide internal standards corresponding to different variant sequences of a single amino acid subsequence of a single protein are provided. A match between a peptide internal standard and a target peptide in a sample indicates the presence of a variant sequence in the sample. In one aspect, the multiple peptide internal standards corresponding to variant sequences are differentially labeled.

In a further aspect, a panel of peptide internal standards corresponding to amino acid subsequences of different proteins in a molecular pathway is generated. Molecular pathways, include, but are not limited to signal transduction pathways, cell cycle pathways, metabolic pathways, blood clotting pathways, and the like. In one aspect, the panel includes peptide standards which correspond to different modified forms of one or more proteins in a pathway and the panel is used to determine the presence and/or quantity of the activated or inactivated form of a pathway protein.

The invention also provides a method for determining the presence and/or quantity of a target polypeptide in at least one mixture of different polypeptides. The method comprises providing a mixture of different polypeptides and spiking the mixture with a known quantity of a peptide internal standard labeled with a mass-altering label. Preferably, the labeled peptide internal standard comprises a subsequence of the target polypeptide and possesses a known peptide fragment signature diagnostic of the presence of the peptide subsequence. The spiked mixture is treated with a protease activity to generate a plurality of peptides including the labeled peptide internal standard and peptides corresponding to the target polypeptide. Preferably, a chromatographic separation step is performed to isolate the labeled peptide internal standard and any target peptide present in the spiked mixture which comprises the same amino acid sequence as the standard. Preferably, the internal standard and target peptide co-elute with each other.

The labeled peptide internal standard and target peptide are fragmented (e.g., using multistage mass spectrometry) and the ratio of labeled fragments to unlabeled fragments; is determined. The quantity of the target polypeptide can be calculated using both the ratio and known quantity of the labeled internal standard. The mixtures of different polypeptides can include, but are not limited to, such complex mixtures as a crude fermenter solution, a cell-free culture fluid, a cell or tissue extract, blood sample, a plasma sample, a lymph sample, a cell or tissue lysate; a mixture comprising at least about 100 different polypeptides; at least about 1000 different polypeptides, at least about 100,000 different polypeptides. or a mixture comprising substantially the entire complement of proteins in a cell or tissue. In one preferred aspect, the method is used to determine the presence of and/or quantity of one or more target polypeptides directly from one or more cell lysates, i.e., without separating proteins from other cellular components or eliminating other cellular components.

In one aspect, the presence and/or quantity of target polypeptide in a mixture are diagnostic of a cell state. In another aspect, the cell state is representative of an abnormal physiological response, for example, a physiological response which is diagnostic of a disease. In a further aspect, the cell state is a state of differentiation or represents a cell which has been exposed to a condition or agent (e.g., a drug, a therapeutic agent, a potential toxin). In one aspect, the method is used to diagnose the presence or risk of a disease. In another aspect, the method is used to identify a condition or agent which produces a selected cell state (e.g., to identify an agent which returns one or more diagnostic parameters of a cell state to normal).

In a further aspect, the method comprises determining the presence and/or quantity of target peptides in at least two mixtures. In another aspect, one mixture is from a cell having a first cell state and the second mixture is from a cell having a second cell state. In a further aspect, the first cell is a normal cell and the second cell is from a patient with a disease. In still a further aspect, the first cell is exposed to a condition and/or treated with an agent and the second cell is not exposed and/or treated. Preferably, first and second mixtures are evaluated in parallel.

Alternatively, the two mixtures can be from identical samples or cells. In one aspect, a labeled peptide internal standard is provided in different known amounts in each mixture. In another aspect, pairs of labeled peptide internal standards are provided each comprising mass-altering labels which differ in mass, e.g., by including different amounts of a heavy isotope in each peptide.

The invention also provides a method of determining the presence of and/or quantity of a modification in a target polypeptide. Preferably, the label in the internal standard is part of a peptide comprising a modified amino acid residue or to an amino acid residue which is predicted to be modified in a target polypeptide. In one aspect, the presence of the modification reflects the activity of a target polypeptide and the assay is used to detect the presence and/or quantity of an active polypeptide. The method is advantageous in enabling detection of small quantities of polypeptide (e.g., about 1 part per million (ppm) or less than about 0.001% of total cellular protein).

The invention additionally provides a method for scanning for mutations in a protein sequence using panels of peptide internal standards corresponding to different variant forms of a single sequence or multiple peptide internal standards representing different amino acid subsequences of a protein. In the first scenario, a match to a variant peptide internal standard in a sample indicates the presence of the variant in the sample. In the second scenario, a lack of match to a one peptide internal standard and matches to one or more other peptide internal standards indicates the presence of a mutation in the amino acid sequence corresponding to the mismatched peptide.

In a further aspect, the invention provides a method for profiling the activity of a molecular pathway using panels of peptide internal standards corresponding to different pathway proteins and/or to different modified forms of the proteins. The presence and/or quantity of the proteins can be used to profile the function of a pathway in a particular cell. In one aspect, the pathway is one or more of a signal transduction pathway, a cell cycle pathway, a metabolic pathway, a blood clotting pathway and the like. The coordinate function of multiple pathways can be evaluated using a plurality of panels of standards. Similarly, the peptide internal standards can be used to assay for the presence of multiple diseases or pathological conditions by providing a panel of peptide internal standards which comprises peptide internal standards diagnostic of different diseases.

The invention further provides reagents useful for performing the method. In one aspect, a reagent according to the invention comprises a peptide internal standard labeled with a stable isotope. Preferably, the standard has a unique peptide fragmentation signature diagnostic of the peptide. The peptide is a subsequence of a known protein and can be used to identify the presence of and/or quantify the protein in sample, such as a cell lysate. In one aspect, the peptide internal standard comprises a label associated with a modified amino acid residue, such as a phosphorylated amino acid residue, a glycosylated amino acid residue, an acetylated amino acid residue, a farnesylated residue, a ribosylated residue, and the like. In another aspect, a pair of reagents is provided, a peptide internal standard corresponding to a modified peptide and a peptide internal standard corresponding to a peptide identical in sequence but not modified.

In one aspect, panels of peptide internal standards representing different variant forms of a single amino acid subsequence of a polypeptide are provided.

In another aspect, panels of peptide internal standards corresponding to different amino acid subsequences of single polypeptide are provided.

In a further aspect, panels of peptide internal standards are provided which correspond to different proteins in a molecular pathway (e.g., a signal transduction pathway, a cell cycle pathway, a metabolic pathway, a blood clotting pathway and the like). In still a further aspect, peptide internal standards corresponding to different modified forms of one or more proteins in a pathway are provided.

In still a further aspect, panels of peptide internal standards are provided which correspond to proteins diagnostic of different diseases, allowing a mixture of peptide internal standards to be used to test for the presence of multiple diseases in a single assay.

The invention additionally provides kits comprising one or more peptide internal standards labeled with a stable isotope. In one aspect, a kit comprises peptide internal standards comprising different peptide subsequences from a single known protein. In another aspect, the kit comprises peptide internal standards corresponding to different variant forms of the same amino acid subsequence of a target polypeptide. In still another aspect, the kit comprises peptide internal standards corresponding to different known or predicted modified forms of a polypeptide. In a further aspect, the kit comprises peptide internal standards corresponding to sets of related proteins, e.g., such as proteins involved in a molecular pathway (a signal transduction pathway, a cell cycle, etc) and/or to different modified forms of proteins in the pathway. In still a further aspect, a kit comprises a labeled peptide internal standard as described above and software for performing multistage mass spectrometry. The kit may also include a means for obtaining access to a database comprising data files which include data relating to the mass spectra of fragmented peptide ions generated from peptide internal standards. The means for obtaining access can be provided in the form of a URL and/or identification number for accessing a database or in the form of a computer program product comprising the data files. In one aspect, the kit comprises a computer program product which is capable of instructing a processor to perform any of the methods described above.

The invention additionally provides a method for determining a site of ubiquitination. The method comprises obtaining a plurality of ubiquitinated polypeptides, digesting the ubiquitinated polypeptides with a protease, thereby generating a plurality of test peptides, and determining the presence of an isopeptide bond in a test peptide by mass spectrometry, wherein the presence of the bond indicates a site of ubiquitination. The test peptide being evaluated can be ionized and/or fragmented prior to the determining step. Preferably, ionizing is performed by electrospray.

In one aspect, the invention provides a method for determining a site of ubiquitination comprising: obtaining a plurality of ubiquitinated polypeptides, digesting the ubiquitinated polypeptides with a protease, thereby generating a plurality of test peptides, at least some of which comprise a ubiquitin remnant, identifying a mass difference between a test peptide and a reference peptide comprising a known identical amino acid sequence as the test peptide, the mass difference corresponding to the mass of the ubiquitin remnant, wherein detection of the mass difference indicates a site of ubiquitination in the test peptide.

In another aspect, the methods further comprise the step of mapping a sequence of a test peptide comprising a ubiquitin remnant to a polypeptide sequence comprising the same amino acid sequence as the test peptide, thereby determining the site of ubiquitination in the polypeptide sequence. In another aspect, the ubiquitin remnant comprises Gly-Gly amino acid residues and has a mass of about 114 daltons. The methods can be used to detect one or more sites of ubiquitination in a polypeptide, as well as the amount of ubiquitination at particular sites in a population of polypeptides.

The methods also can include the step of determining the presence, site, and/or amount of a protein modification other than ubiquitination.

Ubiquitinated polypeptides can be obtained by contacting cellular polypeptides with binding partners which bind to a ubiquitin molecule thereby forming ubiquitinated polypeptide:binding partner complexes. The complexes can be isolated using standard affinity purification methods. In one aspect, the ubiquitin molecule comprises an affinity tag such as 6x-histidine. The ubiquitinated polypeptides can be obtained from a cell expressing tagged ubiquitin molecules. The cell can be a mammalian cell, e.g., a mouse cell.

In another aspect, the methods further comprise the step of separating the ubiquitinated peptides obtained. Preferably, separating is performed by at least one round of liquid chromatography, such as reversed-phase liquid chromatography or by HPLC.

In a further aspect, ubiquitination sites are identified for a plurality of polypeptides in a first cell and in a second cell and the sites identified in the first cell are compared to those in the second cell. In one aspect, the first cell is a normal cell (e.g., from a healthy patient), while the second cell is from a patient with a pathological condition (e.g., a neurodegenerative disease, cancer, a disease of the immune system). Preferably, the second cell is the target of the pathology (e.g., a tumor cell from a cancer patient; a neural cell from a patient with a neurodegenerative disease). In another aspect, the second cell differs from the first cell in expressing one or more recombinant DNA molecules, but is otherwise genetically identical to the first cell. In a further aspect, the site of ubiquitination is correlated with disease and detection of ubiquitination at the site is associated with risk of the disease. In one aspect, the disease is a neurodegenerative disease, such as Alzheimer's or Pick's disease. In another aspect, the disease is cancer. In a further aspect, the disease is an abnormal immune response or inflammatory disease.

The methods can be used to identify regulators of ubiquitination pathways. In one aspect, the methods further comprise contacting a first cell with a compound and comparing ubiquitination sites identified in the first cell with ubiquitination sites in a second cell not contacted with the compound. The compound may be a therapeutic agent for treating a disease associated with an improper state of ubiquitination (e.g., abnormal sites or amounts of ubiquitination). Suitable agents include, but are not limited to, drugs, polypeptides, peptides, antibodies, nucleic acids (genes, cDNA's, RNA's, antisense molecules, ribozymes, aptamers and the like), toxins, and combinations thereof.

Preferably, the methods further comprise generating a database comprising data files storing information relating to ubiquitination sites for a plurality of polypeptides for a plurality of different cells. Preferably, the data files also include information relating to amount of ubiquitination of a polypeptide in at least one cell. Additionally, the database comprises data relating to the source of the cell (e.g., such as a patient).

The invention further provides a computer memory comprising data files storing information relating to ubiquitination sites for a plurality of polypeptides for a plurality of different cells.

BRIEF DESCRIPTION OF THE FIGURES

The objects and features of the invention can be better understood with reference to the following detailed description and accompanying drawings.

FIG. 3A shows a signature obtained after a second stage of mass spectrometry.

FIG. 4A shows sample processing steps in which a cell lysate is spiked with a known amount of a labeled peptide internal standard according to the invention.

FIG. 5A shows a peptide internal standard suitable for use in detecting and/or quantitating a protein comprising the amino acid sequence GFTALK (SEQ ID NO:2). The upper panel of the Figure shows the native tryptic peptide. The lower portion of the Figure shows a peptide internal standard corresponding to this peptide which comprises a stable isotope ($^{13}C$). As can be seen from the Figure, the stable isotope provides a characteristic mass difference in the two peptides without altering the essential chemical structure of the peptide. FIG. 5B shows a peptide internal standard suitable for use in detecting a phosphorylated form of a protein comprising the amino acid sequence GFTALK (SEC) ID NO:2). FIG. 5C shows a peptide internal standard suitable for use in detecting a methylated form of the amino acid sequence GFTALK (SEQ ID NO:2).

FIG. 9A is a schematic diagram of a signature peptide generated after trypsin digestion of a ubiquitinated polypeptide. FIG. 9B shows an exemplary sequence LIFAGKQLEDGR (SEQ ID NO:7) of a signature peptide produced by trypsin proteolysis. FIG. 9C shows the fragmentation pattern (MS/MS spectrum) acquired for the peptide shown in FIG. 9B.

FIGS. 10A-C show proteins identified comprising multiple ubiquitination sites using methods according to the invention. FIG. 10A shows a table listing of amino acid sequences of poly-ubiquitinated polypeptides. The third column contains amino acid sequences of poly-ubiquitinated polypeptides (line 1 SEQ ID NO: 8 through line 19 SEQ ID NO: 26, numbered consecutively). FIG. 10B shows a table listing ubiquitination sites identified in ubiquitin. The second column contains ubiquitinated signature peptides (line 1 SEQ ID NO: 27 to line 5 SEQ ID NO: 31, numbered consecutively). FIG. 10C shows a list of phosphorylated peptides from candidate ubiquitinated polypeptides. The second column contains amino acid sequences of phosphorylated peptides (line 1 SEQ ID NO: 32 through line 26 SEQ ID NO: 57, numbered consecutively).

DETAILED DESCRIPTION

Figure 1:
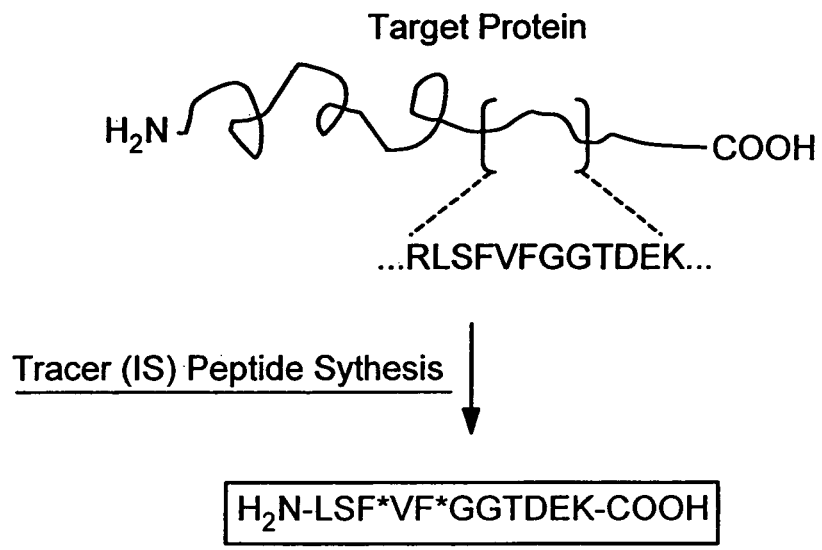
FIG. 1 is a schematic diagram illustrating a method for generating a peptide internal standard (IS) for a protein or modified protein to be detected and/or quantified. The representative IS containing amino acid sequence LSFVFGGTDEK (SEQ ID NO:58) was produced for the corresponding protein (RLSFVFGGTDEK, SEQ ID NO:59).

The invention provides reagents, kits and methods for detecting and/or quantifying proteins in complex mixtures, such as a cell lysate. In one preferred aspect, the proteins comprise one or more modifications. The methods can be used in high through put assays to profile cellular proteomes and to correlate protein modification patterns with particular cell states.

In one aspect, the invention provides a method for determining a site of ubiquitination in a polypeptide and for evaluating ubiquitination targets in a population of polypeptides. In this way, a proteome ubiquitination map can be obtained which comprises information relating to the ubiquitination states of a plurality of cellular polypeptides. Maps can be obtained for a variety of different types of cells and cell states. For example, ubiquitination targets in normal and diseased cells can be evaluated. Preferably, the map is stored as data files in a database. Individual ubiquitinated polypeptides identified can be used to generate molecular probes diagnostic of a cell state and/or can serve as targets for agents which modulate one or more cellular processes.

DEFINITIONS

The following definitions are provided for specific terms which are used in the following written description.

As used in the specification and claims, the singular form "a", "an" and "the" include plural references unless the context clearly dictates otherwise. For example, the term "a cell" includes a plurality of cells, including mixtures thereof. The term "a protein" includes a plurality of proteins.

"Protein", as used herein, means any protein, including, but not limited to peptides, enzymes, glycoproteins, hormones, receptors, antigens, antibodies, growth factors, etc., without limitation. Presently preferred proteins include those comprised of at least 25 amino acid residues, more preferably at least 35 amino acid residues and still more preferably at least 50 amino acid residues. The terms "polypeptide" and "protein" are generally used interchangeably herein to refer to a polymer of amino acid residues.

As used herein, "a polypeptide" refers to a plurality of amino acids joined by peptide bonds. Amino acids can include D-, L-amino acids, and combinations thereof, as well as modified forms thereof. As used herein, a polypeptide is greater than about 20 amino acids. The term "polypeptide" generally is used interchangeably with the term "protein"; however, the term polypeptide also may be used to refer to a less than full-length protein (e.g., a protein fragment) which is greater than 20 amino acids.

As used herein, the term "peptide" refers to a compound of two or more subunit amino acids, and typically less than 20 amino acids. The subunits are linked by peptide bonds.

As used herein, a "target protein" or a "target polypeptide" is a protein or polypeptide whose presence or amount is being determined in a protein sample. The protein/polypeptide may be a known protein (i.e., previously isolated and purified) or a putative protein (i.e., predicted to exist on the basis of an open reading frame in a nucleic acid sequence).

As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be considered "isolated" or "purified."

As used herein, a "protease activity" is an activity which cleaves amide bonds in a protein or polypeptide. The activity may be implemented by an enzyme such as a protease or by a chemical agent, such as CNBr.

As used herein, "a protease cleavage site" is an amide bond which is broken by the action of a protease activity.

As used herein, a "labeled peptide internal standard" refers to a synthetic peptide which corresponds in sequence to the amino acid subsequence of a known protein or a putative protein predicted to exist on the basis of an open reading frame in a nucleic acid sequence and which is labeled by a mass-altering label such as a stable isotope. The boundaries of a labeled peptide internal standard are governed by protease cleavage sites in the protein (e.g., sites of protease digestion or sites of cleavage by a chemical agent such as CNBr). Protease cleavage sites may be predicted cleavage sites (determined based on the primary amino acid sequence of a protein and/or on the presence or absence of predicted protein modifications, using a software modeling program) or may be empirically determined (e.g., by digesting a protein and sequencing peptide fragments of the protein). In one aspect, a labeled peptide internal standard includes a modified amino acid residue.

"Percent identity" and "similarity" between two sequences can be determined using a mathematical algorithm (see, e.g., *Computational Molecular Biology*, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). For example, the percent identity between two amino acid sequences can be determined using the Needleman and Wunsch algorithm (J. Mol. Biol. (48): 444-453, 1970) which is part of the GAP program in the GCG software package (available at http://www.gcg.com), by the local homology algorithm of Smith & Waterman (Adv. Appl. Math. 2: 482, 1981), by the search for similarity methods of Pearson & Lipman (Proc. Natl. Acad. Sci. USA 85: 2444, 1988) and Altschul, et al. (Nucleic Acids Res. 25(17): 3389-3402, 1997), by computerized implementations of these algorithms (GAP, BESTFIT, FASTA, and BLAST in the Wisconsin Genetics Software Package (available from, Genetics Computer Group, 575 Science Dr., Madison, Wis.), or by manual alignment and visual inspection (see, e.g., Ausubel et al., supra). Gap parameters can be modified to suit a user's needs. For example, when employing the GCG software package, a NWSgapdna.CMP matrix and a gap weight of 40, 50, 60, 70, or 80 and a length weight of 1, 2, 3, 4, 5, or 6 can be used. Examplary gap weights using a Blossom 62 matrix or a PAM250 matrix, are 16, 14, 12, 10, 8, 6, or 4, while exemplary length weights are 1, 2, 3, 4, 5, or 6. The percent identity between two amino acid or nucleotide sequences also can be determined using the algorithm of E. Myers and W. Miller (CABIOS 4: 11-17, 1989) which has been incorporated into the ALIGN program (version 2.0), using a PAM120 weight residue table, a gap length penalty of 12 and a gap penalty of 4.

As used herein, "a peptide fragmentation signature" refers to the distribution of mass-to-charge ratios of fragmented peptide ions obtained from fragmenting a peptide, for example, by collision induced disassociation, ECD, LID, PSD, IRNPD, SID, and other fragmentation methods. A peptide fragmentation signature which is "diagnostic" or a "diagnostic signature" of a target protein or target polypeptide is one which is reproducibly observed when a peptide digestion product of a target protein/polypeptide identical in sequence to the peptide portion of a peptide internal standard, is fragmented and which differs only from the fragmentation pattern of the peptide internal standard by the mass of the mass-altering label. Preferably, a diagnostic signature is unique to the target protein (i.e., the specificity of the assay is at least about 95%, at least about 99%, and preferably, approaches 100%).

A "relational" database as used herein means a database in which different tables and categories of the database are related to one another through at least one common attribute and is used for organizing and retrieving data.

The term "external database" as used herein refers to publicly available databases that are not a relational part of the internal database, such as GenBank and Blocks.

As used herein, an "expression profile" refers to measurement of a plurality of cellular constituents that indicate aspects of the biological state of a cell. Such measurements may include, e.g., abundances or proteins or modified forms thereof.

As used herein, a "cell state profile" refers to values of measurements of levels of one or more proteins in the cell. Preferably, such values are obtained by determining the amount of peptides in a sample having the same peptide fragmentation signatures as that of peptide internal standards corresponding to the one or more proteins. A "diagnostic profile" refers to values that are diagnostic of a particular cell state, such that when substantially the same values are observed in a cell, that cell may be determined to have the cell state. For example, in one aspect, a cell state profile comprises the value of a measurement of p53 expression in a cell. A diagnostic profile would be a value which is significantly higher than the value determined for a normal cell and such a profile would be diagnostic of a tumor cell. A "test cell state profile" is a profile which is unknown or being verified.

As used herein, a processor that "receives a diagnostic profile" receives data relating to the values diagnostic of a particular cell state. For example, the processor may receive the values by accessing a database where such values are stored through a server in communication with the processor.

As used herein, a "ubiquitin remnant" is that portion of a ubiquitin protein which remains attached to the digestion product of a polypeptide which has been exposed to a protease.

As used herein, "a binding partner" refers to a first molecule which can form a stable, and specific, non-covalent association with a second molecule to be bound, enabling isolation of the second molecule from a population of molecules including the second molecule. "Stable" refers to an association which is strong enough to permit complexes to form which may be isolated.

As used herein, an "antibody" refers to monoclonal or polyclonal, single chain, double chain, chimeric, humanized, or recombinant antibody, or antigen-binding portion thereof (e.g., F(ab')2 fragments and Fab' fragments).

As used herein, the term "biological sample" refers to any material obtained from a living source, for example, an animal such as a human or other mammal, a plant, a bacterium, a fungus, a protist or a virus. The biological sample can be in any form, including a solid material such as a tissue, cells, a cell pellet, a cell extract, a biopsy, a biological fluid such as urine, blood, saliva, spinal fluid, amniotic fluid, exudate from a region of infection or inflammation, or a mouthwash containing buccal cells.

As used herein, "computer readable media" or a "computer memory" refers to any media that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

Labeled Peptide Internal Standards

The invention provides labeled peptide internal standards for use in determining the presence of, and/or quantifying the amount of, a target protein in a sample which comprises an amino acid subsequence identical to the peptide portion of the internal standard. Peptide internal standards are generated by examining the primary amino acid sequence of a protein and synthesizing a peptide comprising the same sequence as an amino acid subsequence of the protein (see, e.g., FIG. 1). In one aspect, the peptide's boundaries are determined by predicting the cleavage sites of a protease. In another aspect, a protein is digested by the protease and the actual sequence of one or more peptide fragments is determined. Suitable proteases include, but are not limited to one or more of: serine proteases (e.g., such as trypsin, hepsin, SCCE, TADG12, TADG14); metallo proteases (e.g., such as PUMP-1); chymotrypsin; cathepsin; pepsin; elastase; pronase; Arg-C; Asp-N; Glu-C; Lys-C; carboxypeptidases A, B, and/or C; dispase; thermolysin; cysteine proteases such as gingipains, and the like. Proteases may be isolated from cells or obtained through recombinant techniques. Chemical agents with a protease activity also can be used (e.g., such as CNBr).

The target protein can be a known protein or a protein predicted to exist on the basis of an open reading frame in a nucleic acid sequence. Such open reading frames can be identified from a database of sequences including, but not limited to, the GenBank database, EMBL data library, the Protein Sequence Database and PIR-International, SWISS-PROT, The ExPASy proteomics server of the Swiss Institute of Bioinformatics (SIB) and databases described in PCT/US01/25884. Predicted cleavage sites also can be identified through modeling software, such as IVIS-Digest (available at http://prospector.ucsf.edu/). Predicted sites of protein modification also can be determined using software packages such as Scansite, Findmod, NetOGlyc (for prediction of type-O-glycosylation sequences), YinOYang (for prediction of O-beta-GlcNac attachment sites), big-PI Predictor (for prediction of GPI modifications), NetPhos (for prediction of Ser, Thr, and Tyr phosphorylation sites), NMT (for prediction of N-terminal N-myristolation) and Sulfinator (for prediction of tyrosine sulfation sites) which are accessible through http://au.expasy.org/tools/#ptm, for example.

A peptide sequence within a target protein is selected according to one or more criteria to optimize the use of the peptide as an internal standard. Preferably, the size of the peptide is selected to minimize the chances that the peptide sequence will be repeated elsewhere in other non-target proteins. Preferably, therefore, a peptide is at least about 6 amino acids. The size of the peptide is also optimized to maximize ionization frequency. Thus, peptides longer than about 20 amino acids are not preferred. In one aspect, an optimal peptide ranges from about 6 amino acids to about 20 amino acids, and preferably from about 7 amino acids to about 15 amino acids.

A peptide sequence is also selected which is not likely to be chemically reactive during mass spectrometry. Thus, peptide sequences which comprise cysteine, tryptophan or methionine residues are avoided.

Peptides also are selected based on the presence of one or more bonds that preferentially fragment. For example, because peptides will preferentially fragment at proline residues, intense fragment ions may be produced at proline. Therefore in one aspect of the invention, a peptide is selected from a region of a protein comprising a proline amino acid residue.

In another aspect, a peptide is selected from a region of a protein which is not expected or not known to be modified, so that the peptide internal standard can be used to determine the quantity of all forms of the protein. However, in a further aspect, the peptide internal standard does include an amino acid residue which is expected to, or is known to be modified, to provide an internal standard to quantify only the modified form the protein (see, e.g., FIGS. 5B and 5C). Peptide standards representing modified (e.g., FIGS. 5B and 5C) and unmodified forms of a protein (see, e.g., FIG. 5A) can be used together, to determine the extent of protein modification in a particular sample of proteins, i.e., to determine what fraction of the total amount of protein is represented by the modified form.

The peptide is synthesized using one or more labeled amino acids (i.e., the label is actually part of the peptide) or less preferably, labels may be attached after synthesis. By providing the label as part of the peptide (see, e.g., FIGS. 5A-5C), there are minimal differences in the chemical structure of a peptide internal standard and a native peptide obtained from the digestion of a target protein with a protease activity. Further, because the peptide is synthesized, it is unnecessary to separate and/or purify the peptide from other cellular proteins.

Preferably, the label is a mass-altering label. The type of label selected is generally based on the following considerations: The mass of the label should preferably be unique to shift fragment masses produced by MS analysis to regions of the spectrum with low background. The ion mass signature component is the portion of the labeling moiety which preferably exhibits a unique ion mass signature in mass spectrometric analyses. The sum of the masses of the constituent atoms of the label is preferably uniquely different than the fragments of all the possible amino acids. As a result, the labeled amino acids and peptides are readily distinguished from unlabeled amino acids and peptides by their ion/mass pattern in the resulting mass spectrum. In a preferred embodiment, the ion mass signature component imparts a mass to a protein fragment produced during mass spectrometric fragmentation that does not match the residue mass for any of the 20 natural amino acids.

The label should be robust under the fragmentation conditions of MS and not undergo unfavorable fragmentation. Labeling chemistry should be efficient under a range of conditions, particularly denaturing conditions and the labeled tag preferably remains soluble in the MS buffer system of choice. Preferably, the label does not suppress the ionization efficiency of the protein. More preferably, the label does not alter the ionization efficiency of the protein and is not otherwise chemically reactive. Alternatively, or additionally, the label contains a mixture of two or more isotopically distinct species to generate a unique mass spectrometric pattern at each labeled fragment position.

In one preferred aspect, peptide internal standards comprise mass-altering labels which are stable isotopes. In certain preferred embodiments, the method utilizes isotopes of hydrogen, nitrogen, oxygen, carbon, or sulfur. Suitable isotopes include, but are not limited to, $^2H$, $^{13}C$, $^{15}N$, $^{17}O$, $^{18}O$, or $^{34}S$. In another aspect, pairs of peptide internal standards can be provided, comprising identical peptide portions but distinguishable labels, e.g., peptides may be labeled at multiple sites to provide different heavy forms of the peptide). Multiple labeled amino acids may be incorporated in a peptide during the synthesis process. In another aspect, the label is part of a peptide comprising a modified amino acid residue, such as a phosphorylated residue (see, e.g., FIG. 5B), a glycosylated residue, an acetylated residue, a ribosylated residue, or a farnesylated residue, a methlyated residue (see, e.g., FIG. 5C). In this embodiment, pairs or larger sets of peptide internal standards corresponding to modified and unmodified peptides also can be produced. In one aspect, such a pair/set is differentially labeled.

Figure 2:
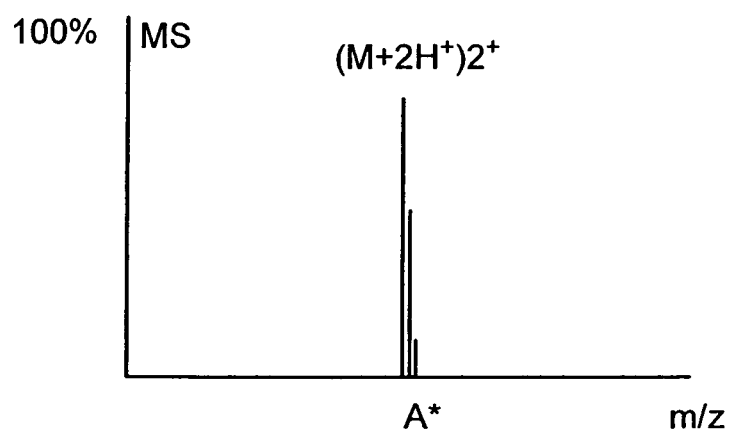
FIG. 2 illustrates characterization of peptide internal standards by mass-to-charge ratio and retention time in reverse phase chromatography according to one aspect of the invention.

Peptide internal standards are characterized according to their mass-to-charge ratio (m/z) and preferably, also according to their retention time on a chromatographic column (e.g., such as an HPLC column). Internal standards are selected which co-elute with peptides of identical sequence but which are not labeled (see, e.g., FIG. 2).

The peptide internal standard is then analyzed by fragmenting the peptide. Fragmentation can be achieved by inducing ion/molecule collisions by a process known as collision-induced dissociation (CID) (also known as collision-activated dissociation (CAD)). Collision-induced dissociation is accomplished by selecting a peptide ion of interest with a mass analyzer and introducing that ion into a collision cell. The selected ion then collides with a collision gas (typically argon or helium) resulting in fragmentation. Generally, any method that is capable of fragmenting a peptide is encompassed within the scope of the present invention. In addition to CID, other fragmentation methods include, but are not limited to, surface induced dissociation (SID) (James and Wilkins, Anal. Chem. 62: 1295-1299, 1990; and Williams, et al., J. Amer. Soc. Mass Spectrom. 1: 413-416, 1990), blackbody infrared radiative dissociation (BIRD); electron capture dissociation (ECD) (Zubarev, et al., J. Am. Chem. Soc. 120: 3265-3266, 1998); post-source decay (PSD), LID, and the like.

The fragments are then analyzed to obtain a fragment ion spectrum. One suitable way to do this is by CID in multistage mass spectrometry ($MS^n$). Traditionally used to characterize the structure of a peptide and/or to obtain sequence information, it is a discovery of the present invention, that $MS^n$ provides enhanced sensitivity in methods for quantitating absolute amounts of proteins. Thus, in one aspect, peptide internal standards are generated for low abundance proteins (e.g., below 2000 copies/cell).

Figure 3A:
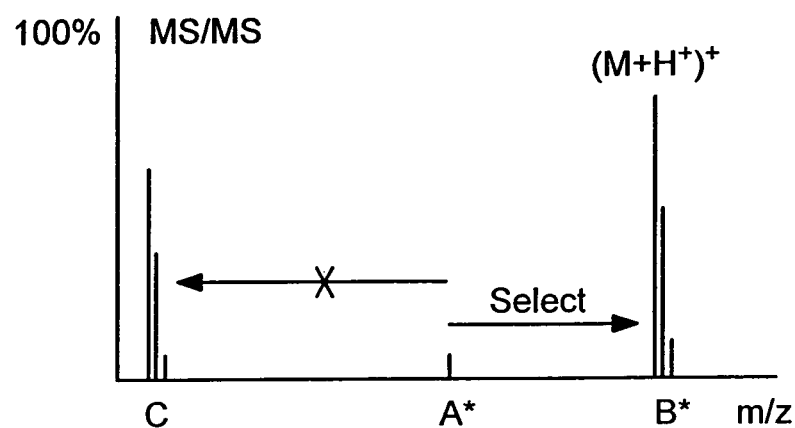
FIGS. 3A and B show characterization of a peptide signature by multistage mass spectrometry.
Figure 3B:
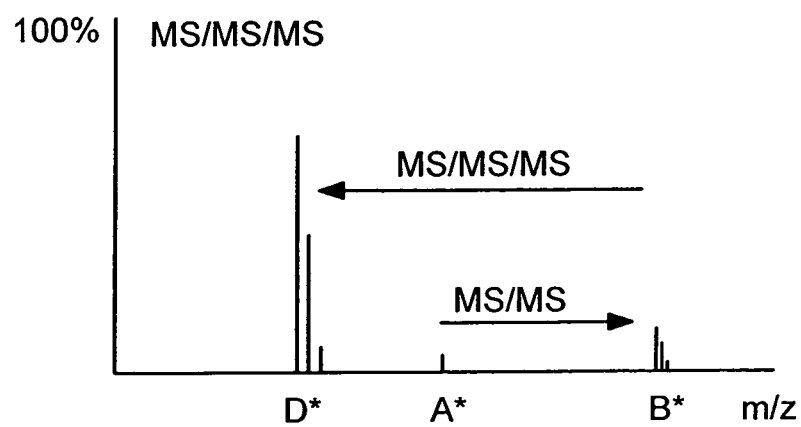
FIG. 3B shows a signature obtained after performing a third stage of mass spectrometry.

Preferably, a peptide internal standard is analyzed by at least two stages of mass spectrometry to determine the fragmentation pattern of the peptide and to identify a peptide fragmentation signature (see, e.g., FIG. 3A). More preferably, a peptide signature is obtained in which peptide fragments have significant differences in m/z ratios to enable peaks corresponding to each fragment to be well separated. Still more preferably, signatures are unique, i.e., diagnostic of a peptide being identified and comprising minimal overlap with fragmentation patterns of peptides with different amino acid sequences. If a suitable fragment signature is not obtained at the first stage, additional stages of mass spectrometry are performed until a unique signature is obtained (see, e.g., FIG. 3B).

Fragment ions in the MS/MS and $MS^3$ spectra are generally highly specific and diagnostic for peptides of interest. In contrast, to prior art methods, the identification of peptide diagnostic signatures provides for a way to perform highly selective analysis of a complex protein mixture, such as a cellular lysate in which there may be greater than about 100, about 1000, about 10,000, or even about 100,000 different kinds of proteins. Thus, while conventional mass spectroscopy would not be able to distinguish between peptides with different sequences but similar m/z ratios (which would tend to co-elute with any labeled standard being analyzed), the use of peptide fragmentation methods and multistage mass spectrometry in conjunction with LC methods, provide a way to detect and quantitate target proteins which are only a small fraction of a complex mixture (e.g., present in less than 2000 copies per cell or less than about 0.001% of total cellular protein) through these diagnostic signatures.

Figure 6:
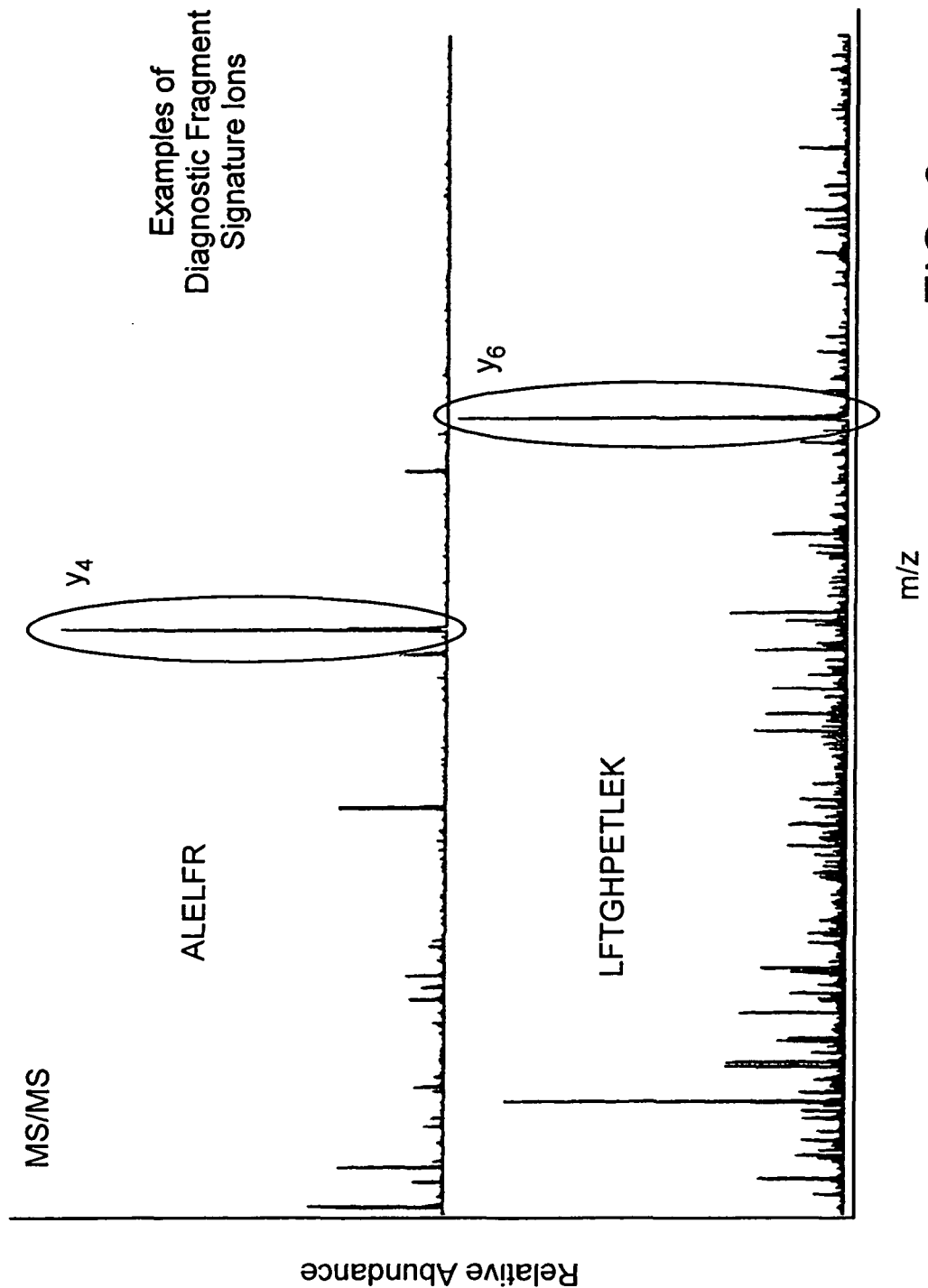
FIG. 6 shows diagnostic peptide fragmentation signatures obtained for two peptides comprising the sequences ALELFR (SEQ ID NO:3) and LFTGHPETLEK (SEQ ID NO:4), respectively, from the myoglobin protein. Each peptide produces a characteristic signature ion that can be used to detect and/or quantify myoglobin in a sample of cellular proteins. Providing both peptide internal standards together in an assay can provide an additional control for quantification.

Multiple peptide subsequences of a single protein may be synthesized, labeled, and fragmented to identify optimal fragmentation signatures. However, in one aspect at least two different peptides are used as internal standards to identify/ quantify a single protein, providing an internal redundancy to any quantitation system (see, e.g., as shown in FIG. 6). In another aspect, peptide internal standards are synthesized which correspond to a single amino acid subsequence of a target polypeptide but which vary in one or more amino acids. The peptide internal standards may correspond to known variants or mutations in the target polypeptide or can be randomly varied to identify all possible mutations in an amino acid sequence.

In one preferred aspect, peptide internal standards corresponding to proteins expressed from nucleic acids comprising single nucleotide polymorphisms are synthesized to identify variant proteins encoded by such nucleic acids. Thus, peptide internal standards can be generated corresponding to SNP's which map to coding regions of genes and can be used to identify and quantify variant protein sequences on an individual or population level. SNP sequences can be accessed through The Human SNP database available at http://www-genome.wi.mit.edu/SNP/human/index.html.

Peptide internal standards may also be used to scan for mutations in proteins including, but not limited to, BRCA1, BRCA2, CFTR, p53, blood group antigens, HLA proteins, MHC proteins, G-Protein Coupled Receptors, apolipoprotein E, kinases (e.g., such as hCds1, MTKs, PTK, CDKs, STKs, CaMs, and the like) (see, e.g., U.S. Pat. No. 6,426,206), phosphatases, human drug metabolizing proteins, viral proteins such as a viral envelope proteins (e.g., HIV envelope proteins), transporter proteins, and the like.

In a further aspect, peptides corresponding to different modified forms of a protein are synthesized, providing internal standards to detect and/or quantitate changes in protein modifications in different cell states. In still a further aspect, peptide internal standards are generated which correspond to different proteins in a molecular pathway and/or modified forms of such proteins (e.g., proteins in a signal transduction pathway, cell cycle, metabolic pathway, blood clotting pathway, etc.) providing panels of internal standards to evaluate the regulated expression of proteins and/or the activity of proteins in a particular pathway. Combinations of the above-described internal standards can be used in a given assay.

Methods of Using Peptide Internal Standards

The labeled peptide internal standards according to the invention can be used to facilitate quantitative determination of the relative amounts of proteins in different samples. Also, the use of differentially isotopically labeled reagents as internal standards facilitates quantitative determination of the absolute amounts of one or more proteins present in a single sample. Samples that can be analyzed by method of the invention include, but are not limited to, cell homogenates; cell fractions; biological fluids, including, but not limited to urine, blood, and cerebrospinal fluid; tissue homogenates; tears; feces; saliva; lavage fluids such as lung or peritoneal lavages; and generally, any mixture of biomolecules, e.g., such as mixtures including proteins and one or more of lipids, carbohydrates, and nucleic acids such as obtained partial or complete fractionation of cell or tissue homogenates.

Preferably, a proteome is analyzed. By a proteome is intended at least about 20% of total protein coming from a biological sample source, usually at least about 40%, more usually at least about 75%, and generally 90% or more, up to and including all of the protein obtainable from the source. Thus, the proteome may be present in an intact cell, a lysate, a microsomal fraction, an organelle, a partially extracted lysate, biological fluid, and the like. The proteome will be a mixture of proteins, generally having at least about 20 different proteins, usually at least about 50 different proteins and in most cases, about 100 different proteins, about 1000 different proteins, about 10,000 different proteins, about 100,000 different proteins, or more. In one aspect, a proteome comprises substantially all of the proteins in a cell. In one preferred aspect, as shown in FIG. 4A, a complex mixture of cellular proteins is evaluated directly from a cell lysate, i.e., without any steps to separate and/or purify and/or eliminate cellular components or cellular debris.

While the methods described herein are compatible with any biochemical, immunological or cell biological fractionation methods that reduce sample complexity and enrich for proteins of low abundance, it is a particular advantage of the method that it can be used to detect and quantitate peptides in complex mixtures of polypeptides, such as cell lysates. Unlike methods in the prior art, because the present invention detects diagnostic signatures that are highly selective for individual peptides, the quantities of such peptides can be discerned even in a mixture of peptides of similar mass/charge ratios.

Generally, the sample will have at least about 0.01 mg of protein, at least about 0.05 mg, and usually at least about 1 mg of protein or 10 mg of protein or more, typically at a concentration in the range of about 0.1-10 mg/ml. The sample may be adjusted to the appropriate buffer concentration and pH, if desired.

Figure 4A:
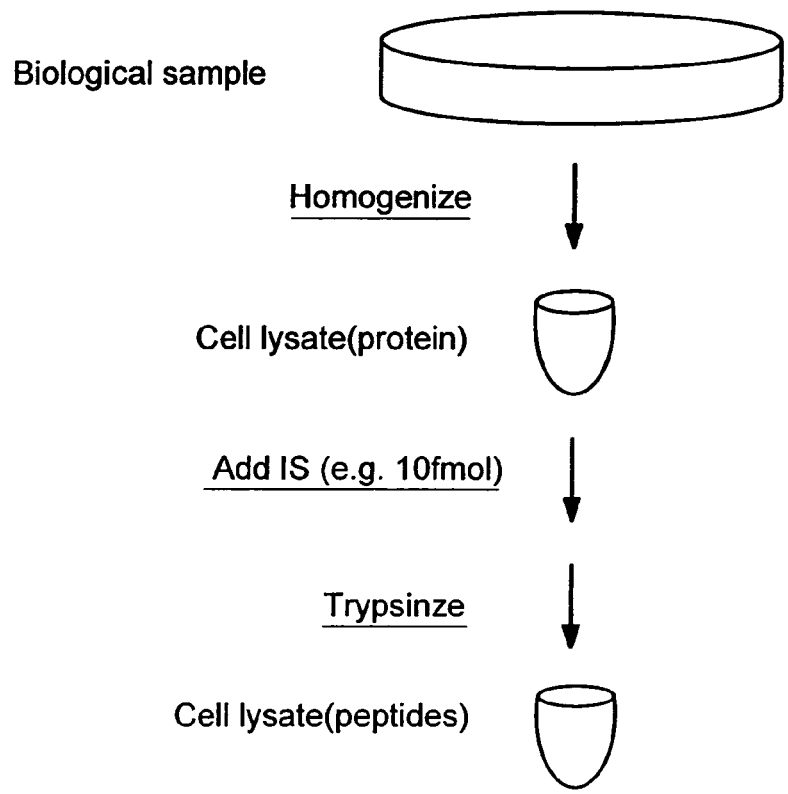
FIGS. 4A and B illustrate steps in a method for absolute quantitation of proteins in a complex mixture of proteins.

In one aspect, as shown in FIG. 4A, a known amount of a labeled peptide internal standard corresponding to a target protein to be detected and/or quantitated, is added to a sample such as a cell lysate. Preferably, about 10 femtomoles is spiked into the sample. The sample is contacted with a protease activity (e.g., one or more proteases or appropriate chemical agent(s) are added to the sample) and the spiked sample is incubated for a suitable period of time to allow peptide digestion. If the target protein is present in the sample, the digestion step should liberate a target peptide identical in sequence to the peptide portion of the internal standard and the amount of target peptides so liberated from target proteins in the sample should be proportional to the amount of target protein in the sample.

Preferably, a separation procedure is performed to separate a labeled peptide internal standard and corresponding target peptide from other peptides in the sample. Representative examples include high-pressure liquid chromatography (HPLC), Reverse Phase-High Pressure Liquid Chromatography (RP-HPLC), electrophoresis (e.g., capillary electrophoresis), anion or cation exchange chromatography, and open-column chromatography. Preferred is microcapillary liquid chromatography. As discussed above, internal standards are selected so that they co-elute with their corresponding target peptides as pairs of peptides that differ only in the mass contributed by the mass-altering label.

Figure 4B:
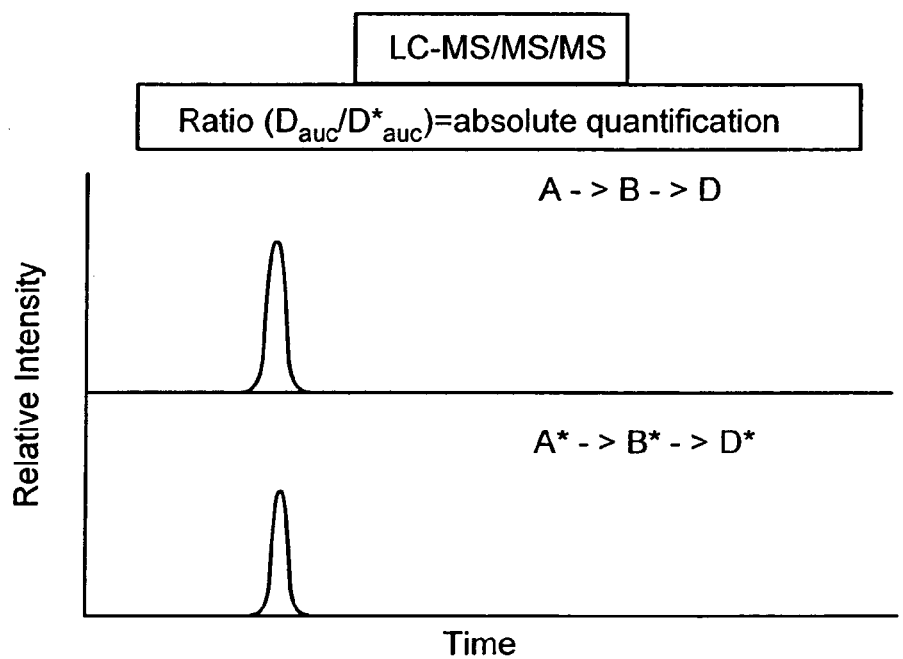
FIG. 4B shows mass spectra of a labeled peptide internal standard and the corresponding unlabeled peptide in the sample. The ratio of labeled to unlabeled peptide provides a means to quantify the amount of unlabeled peptide in the sample.

Each peptide then is examined by monitoring of a selected reaction in the mass spectrometer. This involves using the prior knowledge gained by the characterization of the peptide internal standard and then requiring the mass spectrometer to continuously monitor a specific ion in the MS/MS or MS$^n$ spectrum for both the peptide of interest and the internal standard. After elution, the areas-under-the-curve (AUC) for both the peptide internal standard and target peptide peaks are calculated (see, e.g., FIG. 4B). The ratio of the two areas provides the absolute quantification that can be normalized for the number of cells used in the analysis and the protein's molecular weight, to provide the precise number of copies of the protein per cell.

In one aspect, the presence and/or quantity of target polypeptide in a mixture is diagnostic of a cell state. In another aspect, the cell state is representative of an abnormal physiological response, for example, a physiological response which is diagnostic of a disease. In a further aspect, the cell state is a state of differentiation or represents a cell which has been exposed to a condition or agent (e.g., a drug, a therapeutic agent, a potential toxin). Preferably, protein quantities identified are compared to a reference quantity obtained from a reference sample (e.g., a sample from a normal patient, a sample not exposed to a condition or agent, etc.).

In another aspect, the method comprises determining the presence and/or quantity of target peptides in at least two mixtures. In still another aspect, one mixture is from a cell having a first cell state and the second mixture is from a cell having a second cell state. In a further aspect, the first cell is a normal cell and the second cell is from a patient with a disease. Preferably, first and second mixtures are evaluated in parallel.

Alternatively, the two mixtures can be from identical samples or cells. In one aspect, the labeled peptide internal standard is provided in different known amounts in each mixture. In another aspect, pairs of labeled peptide internal standards are provided each comprising mass-altering labels that differ in mass. For example, differentially labeled peptides may be generated by incorporating different amounts of a heavy label into each peptide varying the number of sites within the peptides labeled by a heavy isotope.

The invention also provides a method of determining the presence of and/or quantity of a modification in a target polypeptide. Preferably, the label in the internal standard is attached to a peptide comprising a modified amino acid residue or to an amino acid residue that is predicted to be modified in a target polypeptide. In one aspect, multiple internal standards representing different modified forms of a single protein and/or peptides representing different modified regions of the protein are added to a sample and corresponding target peptides (bearing the same modifications) are detected and/or quantified. Preferably, standards representing both modified and unmodified forms of a protein are provided in order to compare the amount of modified protein observed to the total amount of protein in a sample.

In another aspect, peptide internal standards comprising different peptides from a single protein are added in known amounts to a sample to provide additional controls or to scan for mutations in different regions of a protein. In a further aspect, peptides corresponding to a single amino acid subsequence in a protein but representing different variant forms of the protein are added to a sample as a means of detecting and/or quantifying a particular variant form of the protein.

In still another aspect, peptide internal standards are added to a sample that represents different proteins in a molecular pathway (e.g., a signal transduction pathway, a cell cycle, a metabolic pathway, a blood clotting pathway) and/or different modified forms of such proteins. In this aspect, the function of the pathway is evaluated by monitoring the presence, absence or quantity of particular pathway proteins and/or their modified forms. Multiple pathways may be evaluated at a time by combining mixtures of different pathway peptide internal standards.

In a further aspect, peptide internal standards represent proteins and/or modified forms thereof whose presence is diagnostic of a particular tissue type (e.g., neural proteins, cardiac proteins, skin proteins, lung proteins, liver proteins, pancreatic proteins, kidney proteins, proteins characteristic of reproductive organs, etc.). These can be used separately or in combination to perform tissue-typing analysis.

Peptide internal standards may represent proteins or modified forms thereof whose presence is characteristic of a particular genotype (e.g., such as HLA proteins, blood group proteins, proteins characteristic of a particular pedigree, etc.). These can be used separately or in combination to perform forensic analyses, for example.

In one aspect, peptide internal standards are used in prenatal testing to detect the presence of a congenital disease or to quantitate protein levels diagnostic of a chromosomal abnormality.

Peptide internal standards may represent proteins or modified forms thereof whose presence is characteristic of particular diseases. Such peptides may correspond to target proteins diagnostic of neurological disease (e.g., neurodegenerative diseases, including, but not limited to, Alzheimer's disease; amyotrophic lateral sclerosis; dementia, depression; Down's syndrome; Huntington's disease; peripheral neuropathy; multiple sclerosis; neurofibromatosis; Parkinson's disease; and schizophrenia). These standards can be used separately or in combination to diagnose a neurological disease.

Preferably, sets of internal standards are used so that diagnostic fragmentation signatures can be evaluated for a number of different diseases in a single assay. Thus, a sample may be obtained from a patient who presents with general symptoms associated with a neurological disease, and a peptide internal standard mixture comprising internal standards for proteins diagnostic of different neurological diseases can be added to the sample. The sample is contacted with a protease activity and peptide fractions are obtained, e.g., such as by HPLC. Peptide ions are subsequently fragmented as described above to detect any diagnostic fragmentation signatures present characteristic of a particular disease. The uniqueness of the fragmentation signature thus allows a specific diagnosis to be obtained while testing for a plurality of different types of diseases. The peptide internal standard mixture may include a peptide internal standard corresponding to a control target protein, such as a constitutively expressed protein of known abundance. A negative standard (e.g., such as a peptide internal standard corresponding to a plant protein) may also be provided.

Similarly, peptide internal standards can be used to diagnose an immune disease, including, but not limited to, acquired immunodeficiency syndrome (AIDS); Addison's disease; adult respiratory distress syndrome; allergies; ankylosing spondylitis; amyloidosis; anemia; asthma; atherosclerosis; autoimmune hemolytic anemia; autoimmune thyroiditis; bronchitis; cholecystitis; contact dermatitis; Crohn's disease; atopic dermatitis; dermatomyositis; diabetes mellitus; emphysema; episodic lymphopenia with lymphocytotoxins; erythroblastosis fetalis; erythema nodosum; atrophic gastritis; glomerulonephritis; Goodpasture's syndrome; gout; Graves' disease; Hashimoto's thyroiditis; hypereosinophilia; irritable bowel syndrome; myasthenia gravis; myocardial or pericardial inflammation; osteoarthritis; osteoporosis; pancreatitis; and polymyositis.

Similarly, peptide internal standards can be used to characterize infectious diseases, respiratory diseases, reproductive diseases, gastrointestinal diseases, dermatological diseases, hematological diseases, cardiovascular diseases, endocrine diseases, urological diseases, and the like.

Because peptide internal standards provide diagnostic fragmentation signatures for detecting and/or quantitating proteins or modified forms thereof, changes in the presence or amounts of such fragmentation signatures in a sample of proteins from a cell (e.g., such as a cell lystate), as discussed above, can be diagnostic of a cell state. In one aspect, a single fragmentation signature from a peptide internal standard is diagnostic. In other aspects, sets of fragmentation signatures are diagnostic and multiple peptide internal standards are spiked into a sample to evaluate changes in cell state.

In one preferred embodiment, changes in cell state are evaluated after exposure of the cell to a compound. Compounds are selected which are capable of normalizing a cell state, e.g., by selecting for compounds which alter fragmentation signatures from those characteristic of abnormal physiological responses to those representative of a normal cell.

For example, a three-way comparison of healthy, diseased, and treated diseased individuals can identify which compounds are able to restore a disease cell state to a one that more closely resembles a normal cell state. This can be used to screen for drugs or other therapeutic agents, to monitor the efficacy of treatment, and to detect or predict the occurrence of side effects, whether in a clinical trial or in routine treatment, and to identify protein targets which are more important to the manifestation and treatment of a disease.

Compounds which can be evaluated include, but are not limited to: drugs; toxins; proteins; polypeptides; peptides; amino acids; antigens; cells, cell nuclei, organelles, portions of cell membranes; viruses; receptors; modulators of receptors (e.g., agonists, antagonists, and the like); enzymes; enzyme modulators (e.g., such as inhibitors, cofactors, and the like); enzyme substrates; hormones; nucleic acids (e.g., such as oligonucleotides; polynucleotides; genes, cDNAs; RNA; antisense molecules, ribozymes, aptamers), and combinations thereof. Compounds also can be obtained from synthetic libraries from drug companies and other commercially available sources known in the art (e.g., including, but not limited, to the LeadQuest® library) or can be generated through combinatorial synthesis using methods well known in the art. In one aspect, a compound is identified as a modulating agent if it alters the site of modification of a polypeptide and/or if it alters the amount of modification by an amount that is significantly different from the amount observed in a control cell (e.g., not treated with compound) (setting p values to <0.05). In another aspect, a compound is identified as a modulating agent, if it alters the amount of the polypeptide (whether modified or not).

Compounds identified as modulating agents are used in methods of treatment of pathologies associated with abnormal sites/levels of modification or abnormal levels or types of protein. For administration to a patient, one or more such compounds are generally formulated as a pharmaceutical composition. Preferably, a pharmaceutical composition is a sterile aqueous or non-aqueous solution, suspension or emulsion, which additionally comprises a physiologically acceptable carrier (i.e., a non-toxic material that does not interfere with the activity of the active ingredient). More preferably, the composition also is non-pyrogenic and free of viruses or other microorganisms. Any suitable carrier known to those of ordinary skill in the art may be used. Representative carriers include, but are not limited to: physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Routes and frequency of administration, as well doses, will vary from patient to patient. In general, the pharmaceutical compositions is administered intravenously, intraperitoneally, intramuscularly, subcutaneously, intracavity or transdermally. Between 1 and 6 doses is administered daily. A suitable dose is an amount that is sufficient to show improvement in the symptoms of a patient afflicted with a disease associated an aberrant modification state or an abnormal level or type of a protein. Such improvement may be detected by monitoring appropriate clinical or biochemical endpoints as is known in the art. In general, the amount of a modulating agent present in a dose, or produced in situ by DNA present in a dose (e.g., where the modulating agent is a polypeptide or peptide encoded by the DNA), ranges from about 1 µg to about 100 mg per kg of host. Suitable dose sizes will vary with the size of the patient, but will typically range from about 10 mL to about 500 mL for 10-60 kg animal. A patient can be a mammal, such as a human, or a domestic animal.

Detection and Quantitation of Protein Modifications: Identifying Protein Ubiquitination Sites Protein ubiquitination is the most common of all posttranslational modifications. Ubiquitin is a highly conserved 76 amino acid protein which is linked to a protein target after a cascade of transfer reactions. Ubiquitin is activated through the formation of a thioester bond between its C-terminal glycine and the active site cysteine of the ubiquitin activating protein, E1 (Hershko, 1991, *Trends Biochem. Sci.* 16(7): 265-8). In subsequent trans-thiolation reactions, Ubiquitin is transferred to a cysteine residue on a ubiquitin conjugating enzyme, E2 (Hershko, et al., 1983, *J. Biol. Chem.* 267: 8807-8812). In conjunction with E3, a ubiquitin polypeptide ligase, E2 then transfers ubiquitin to a specific polypeptide target (see, e.g., Scheffner, et al., 1995, *Nature* 373(6509): 81-3), forming an isopeptide bond between the C-terminal glycine of ubiquitin and the ε-amino group of a lysine present in the target.

The covalent attachment of ubiquitin to cellular polypeptides, in most cases, marks them for degradation by a multi-polypeptide complex called a proteosome. The ubiquitin-proteosome system is the principal mechanism for the turnover of short-lived polypeptides, including regulatory polypeptides (Weissman, 2001, *Nat. Rev. Mol. Cell. Biol.* 2: 169-78). Some known targets of ubiquitination include: cyclins, cyclin-dependent kinases (CDK's), NFkβ, cystic fibrosis transduction receptor, p53, ornithine decarboxylase (ODC), 7-membrane spanning receptors, Cdc25 (phosphotyrosme phosphatase), Rb, Gα, c-Jun and c-Fos. Polypeptides sharing consensus sequences such as PEST sequences, destruction boxes, and F-boxes generally are also targets for ubiquitin-mediated degradation pathways (see, e.g., Rogers, et al., 1986, *Science* 234: 364-368; Yamano, et al., 1998, *The EMBO Journal* 17: 5670-5678; Bai, et al., 1996, *Cell* 86: 263-274).

Ubiquitin has been implicated in a number of cellular processes including: signal transduction, cell-cycle progression, receptor-mediated endocytosis, transcription, organelle biogenesis, spermatogenesis, response to cell stress, DNA repair, differentiation, programmed cell death, and immune responses (e.g., inflammation). Ubiquitin also has been implicated in the biogenesis of ribosomes, nucleosomes, peroxisomes and myofibrils. Thus, ubiquitin can function both as signal for polypeptide degradation and as a chaperone for promoting the formation of organelles (see, e.g., Fujimuro, et al., 1997, *Eur. J. Biochem.* 249: 427-433).

Deregulation of ubiquitination has been implicated in the pathogenesis of many different diseases. For example, abnormal accumulations of ubiquitinated species are found in patients with neurodegenerative diseases such as Alzheimer's as well as in patients with cell proliferative diseases, such as cancer (see, e.g., Hershko and Ciechanover, 1998, *Annu. Rev. Biochem.* 67: 425-79; Layfield, et al., 2001, *Neuropathol. Appl. Neurobiol.* 27:171-9; Weissman, 1997, *Immunology Today* 18(4): 189).

While the importance of its biological role is well appreciated, the ubiquitin pathway is inherently difficult to study. Generally, studies of ubiquitination have focused on particular polypeptides. For example, site-directed mutagenesis has been used to evaluate critical amino acids which form the "destruction boxes", or "D-boxes", of cyclin, sites which are rapidly poly-ubiquitinated when cyclin is triggered for destruction. See, e.g., Yamano, et al., 1998, *The EMBO Journal* 17: 5670-5678; Amon et al., 1994, *Cell* 77: 1037-1050; Glotzer, et al., 1991, *Nature* 349: 132-138; King, et al., 1996, *Mol. Biol. Cell* 7:1343. Corsi, et al., 1997, *J. Biol. Chem.* 272(5): 2977-2883, describe a Western blotting approach to identify ubiquitination sites in α-spectrin. In this technique, crude radiolabeled α-spectrin fractions were ubiquitinated in vitro, digested with proteases, and electrophoresed on gels. Ubiquitinated peptides were identified by their differences in mass from peptides generated by digestion of non-ubiquitinated α-spectrin.

Identification of Sites of Ubiquitination

In one aspect, the invention provides a method comprising obtaining a test peptide and identifying a site of an isopeptide bond within the peptide, e.g., such as is formed between the terminal C-Gly group of a ubiquitin molecule and the ε-amino group of a lysine residue within the peptide. Preferably, the test peptide is obtained from a ubiquitinated polypeptide which has been digested by a protease (e.g., such as trypsin) to generate a plurality of digestion products, i.e., a plurality of test peptides, one or more of which comprise(s) a remnant of a ubiquitin molecule (e.g., a fragment of ubiquitin refractory to the digestion process). For example, a digested poly-ubiquitinated polypeptide will generate a plurality of test peptides comprising isopeptide bonds, while a mono-ubiquitinated polypeptide will generate only one test peptide which comprises an isopeptide bond.

Digested peptides are purified to isolate individual test peptides for analysis. Preferably, the presence of an isopeptide bond in a test peptide is detected by comparing the mass of the test peptide with the mass of a reference peptide in a panel of non-ubiquitinated peptides of known sequence. A reference peptide is "matched" to a test peptide when it is smaller than the test peptide by the amount of mass characteristic of the ubiquitin remnant. For example, for a trypsin-digested ubiquitinated polypeptide, a test peptide comprising a ubiquitination site will comprise a ubiquitin remnant comprising a Gly-Gly residue, and a mass difference of approximately 114 daltons.

A match to a reference peptide indicates that the test peptide has the same sequence as the reference peptide. The peptide can then be mapped to the polypeptide sequence from which it is derived, either directly, or after determining the masses/sequences of other test peptides which have resulted from the digestion of the ubiquitinated polypeptide. In this way the site of ubiquitination on the polypeptide can be determined.

Isolating Ubiquitinated Polypeptides

Ubiquitinated polypeptides can be isolated by a variety of methods. For example, cellular polypeptides can be contacted with binding partners that bind to a ubiquitin molecule. A ubiquitinated polypeptide:binding partner complex forms which can be isolated through affinity purification of the binding partner. A binding partner can be selected which binds directly to ubiquitin, or which binds to a molecule linked to ubiquitin.

The binding partner can comprise an antibody which binds to ubiquitin. Anti-ubiquitin antibodies are commercially available, and include both polyclonal (e.g., available from Research Diagnostics, Inc., Flanders, N.J.) and monoclonal antibodies (e.g., available from International Biosciences, Inc., Tokyo, Japan). In one aspect, the antibody binds to a ubiquitinated polypeptide but not to free ubiquitin. Such an antibody can be obtained from Signet Antibodies, Inc., Dedham, Mass., for example. In another aspect, the antibody binds to a poly-ubiquitinated polypeptide, but not to free ubiquitin and not to a mono-ubiquitinated polypeptide. Antibodies of this type are commercially available from Affiniti Research, Ltd. (Mamhead Castle, United Kingdom), for example. Additional antibodies can be generated using methods well known in the art (see, e.g., Harlow and Lane, In *Antibodies: A Laboratory Manual*, Cold Spring Harbor Laboratory Press, Cold Spring Harbor, N.Y.).

The antibody preferably is stably associated with a solid phase (e.g., a bead, micro particle, sphere, chip, support, and the like). Antibodies can be linked directly to a solid phase (e.g., chemically conjugated) or can be bound to the solid phase via other binding partners specific for the antibodies immobilized on the solid phase. By contacting a population of polypeptides (e.g., from a cell extract) to the support, ubiquitinated polypeptide: antibody complexes can be isolated. Ubiquitinated polypeptides can be separated from the antibodies using suitable washing conditions known in the art.

Alternatively, or additionally, ubiquitinated polypeptides can be isolated by linking ubiquitin to an affinity tag. As used herein, an "affinity tag" refers to a molecule which facilitates the purification of a polypeptide (e.g., ubiquitin) to which it is attached. In one aspect, the affinity tag is a poly-histidine tract (e.g., a tract of about 6-10 histidines) fused in frame to a ubiquitin molecule. A histidine-tagged ubiquitin molecule can be isolated by contacting a population of peptides, some of which are ubiquitinated, to a solid phase comprising a binding molecule which forms a stable association with histidine (e.g., such s a nickel chelate). Bound molecules comprising ubiquitinated polypeptides are separated from non-bound molecules and ubiquitinated polypeptides are removed from the solid phase using suitable washing conditions.

Ubiquitin conjugates comprising affinity tags can be introduced into cells using methods known in the art; e.g., transfection, electroporation, microinjection, germline transfer, and the like. In one aspect, a transgenic animal expressing ubiquitin conjugates in one or more cells is used as a source of ubiquitinated polypeptides. For example, a mouse expressing histidine-tagged ubiquitin can be used (see, e.g., Tsirigotis, et al., 2001, *Biotechniques* 31: 120-130).

The isolation step described above will not result in the purification of polypeptide fragments or peptides obtained after proteosomal processing, since digested ubiquitin molecules will not be recognized by the binding partners described above. Thus, cellular ubiquitinated polypeptides that are degraded extremely rapidly, i.e., such that essentially little or no ubiquitinated polypeptides accumulate, may not be detected by this method. However, these polypeptides can be examined in a cellular background deficient for the activity or expression of one or more proteosomal polypeptides, i.e., a cell treated with one or more proteasome inhibitors, enabling the degradation process to be uncoupled from the ubiquitination process. Preferably, the proteasome inhibitor is specific to the proteosome rather than acting generally on cellular proteases. Suitable proteosome inhibitors include, but are not limited to, epoxyomycin, lactacystin, 4-hydroxy-5-iodo-3-nitrophenylacetyl-Leu-Leu-leucinal-vinyl sulfone, and the like. Novel inhibitors also may be identified using methods known in the art, e.g., such as described in PCT/US98/14638 9904033.

Obtaining Test Peptides

In one aspect, ubiquitinated polypeptides which are obtained are digested with a protease to generate sets of test peptides, each set corresponding the digestion products of a particular ubiquitinated polypeptide. Suitable proteases are those which do not cleave isopeptide bonds and include, but are not limited to, one or more of: serine proteases (e.g., such as trypsin, hepsin, SCCE, TADG12, TADG14); metallo proteases (e.g., such as PUMP-1); chymotrypsin; cathepsin; pepsin; elastase; pronase; Arg-C; Asp-N; Glu-C; Lys-C; carboxypeptidases A, B, and/or C; dispase; thermolysin; and the like. Generally, the type of protease is not limiting; however, preferably, the protease is an extracellular protease.

Creating this highly complex peptide mixture is straightforward. In one aspect, a population of ubiquitinated polypeptides (e.g., from a cellular extract) is solubilized in a highly reducing and denaturing environment (e.g., 8M urea, 10 mM dithiothreitol (DTT), 50 mM Tris-HCL, pH 8.3). Cysteinyl residues can be alkylated, if desired, and the polypeptide mixture is diluted (e.g., about 8-fold) in the presence of one or more proteases for digestion (e.g., approximately overnight).

Preferably, digestion products are purified to obtain individual test peptides which are substantially isolated from other test peptides (e.g., test peptides which comprise less than 5% of other test peptides, or which comprise greater than about 95% identical peptides). A number of separation strategies can be used, such as gel-based strategies (e.g., 2D-electrophoresis) or liquid chromatography. Liquid chromatography is preferred because it can be integrated readily with subsequent peptide analysis steps, maximizing the throughput of the analysis.

Liquid chromatography (LC) may be used to separate and/or concentrate peptides based on one or more of: their adsorption characteristics, affinity characteristics, ionic properties, and/or size. Suitable LC methods include, but are not limited to: on-line reversed phase liquid chromatography; nano-scale microcapillary reverse-phase chromatography; high pressure liquid chromatography (HPLC); capillary electrophoresis; micro-column liquid chromatography; multidimensional electrophoresis; and the like (see, e.g., Deterding, et al., 1991, *J. Chromatogr.* 554: 73-82; Guo et al., 1988, *Anal Biochem* 168: 54; U.S. Pat. No. 5,496,460; Matson, et al., 1984, *Clin. Chem* 30/9: 1477-1488). One or more separation systems can be combined.

Figure 7:
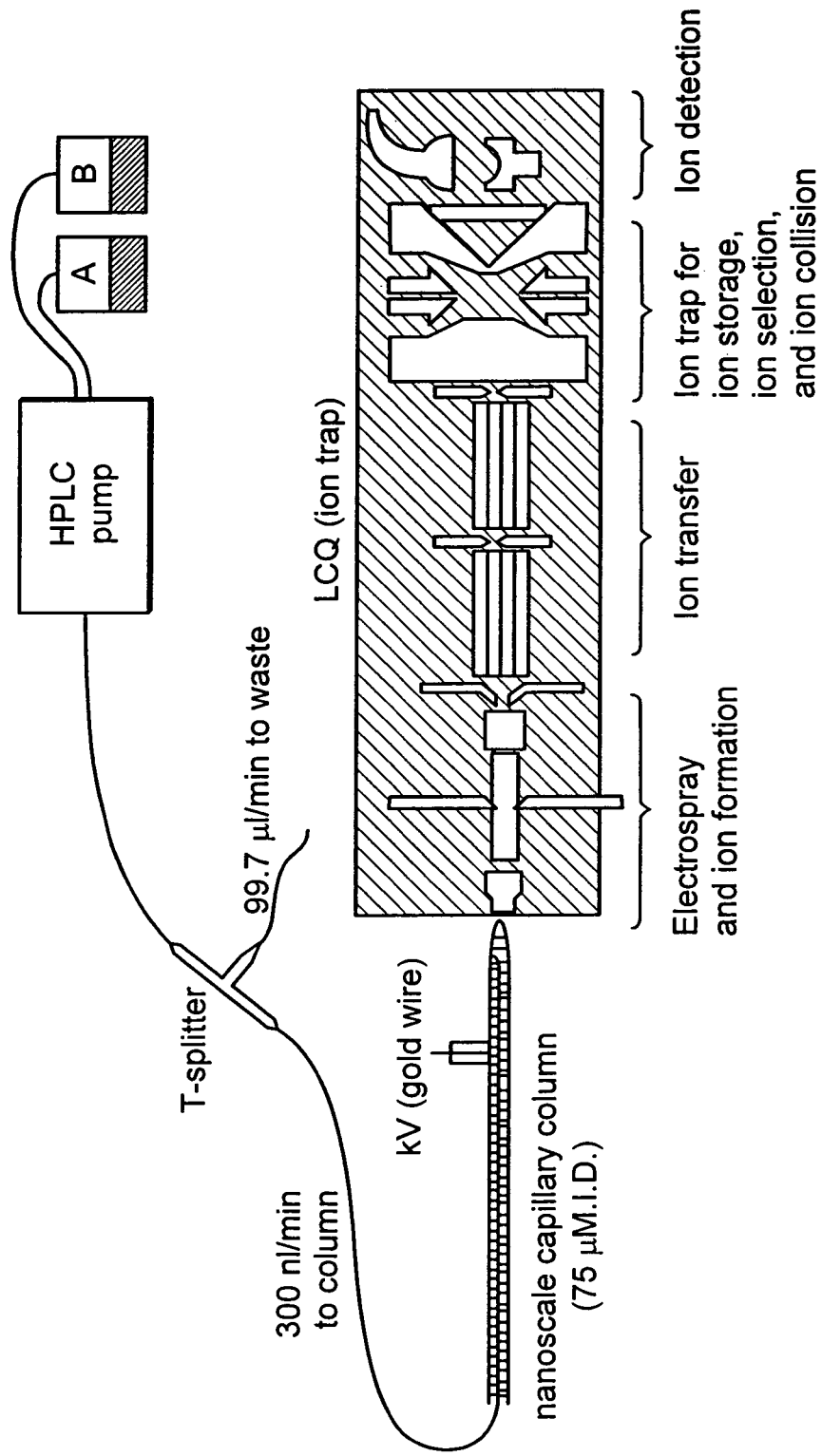
FIG. 7 shows a schematic of an on-line nanoscale microcapillary LC/MS/MS system used in one aspect of the invention.

Preferably, a separation system used in a method according to the invention is one that can be coupled to a peptide analyzer such as a mass spectrometer (MS). In one aspect, the separation system comprises one or more of a pump or sample injector for delivering a sample of ubiquitinated polypeptides; transfer tubing; a pre-column flow splitter for controlling the rate of flow and/or establishing a flow gradient; a capillary column for performing the separation; and a delivery mechanism for delivering substantially purified test peptides to the peptide analyzer (see, e.g., as shown in FIG. 7). The delivery mechanism can comprise a liquid junction, e.g., such as a gold wire at high voltage (1-2 kV), which can be used to promote electrospray. Preferably, a processor is used to control flow of fluids through both the separation system and the peptide analyzer, to coordinate the separation process with the analysis process. For example, elution of a test peptide from the separation column can be synchronized with ionization by a mass spectrometer.

Both column sizes and flow rates in the separation system can be optimized to suit a particular separation. In one aspect, the separation system comprises a capillary column comprising fused-silica tubing and is packed with C18 silica beads. In another aspect, the capillary comprises an about 75 μm internal diameter with about 5 μm of C18 beads and a bed length of about 12 cm.

Flow rates through different portions of the separation device can vary. In one aspect, a pump provides sample to a capillary column at a flow rate of about 100 μl/minute, while the flow rate through the column itself is maintained at approximately 300 nl/min using a column size of approximately 75 μm in internal diameter. A flow restrictor can be used to permit a gradient of flow rates to be formed quickly.

It should be obvious to those of skill in the art that the column dimensions and flow rates described above are exemplary and are not intended to be limiting. Chromatographic parameters can be optimized using methods routine in the art, e.g., through empirical testing and/or computer simulations. For example, a simulation program for optimizing HPLC parameters is described by Dolan, et al., 1987, *Chromatographia* 24: 261-276. Further, a processor may be provided which can monitor and optimize conditions in the separation system. In one aspect, the system processor comprises an expert system which is responsive to signals generated by sensors coupled to various columns and pumps of the systems. The expert system can be used to modulate flow rates, pH, and/or ionic conditions in the separation system in response to feedback from the sensors. Such an expert system is described in U.S. Pat. No. 5,039,409, for example.

A sample can be loaded and eluted in the separation system in different ways depending on the peptide concentration and volume. For example, a sample can be loaded through an injection loop on a valve (e.g., such as a six-port valve) inserted between a T-splitter and a separation column (e.g., a microcapillary). Loading also can be performed off-line via a pressure cell. While this latter approach maximizes sensitivity, more sample handling is required. To increase throughput, sample can be loaded into a pre-column trap for concentration and rapid desalting and then eluted onto the separation column (e.g., such as a reverse phase separation column). Preferably, flow rates in the pre-column trap are on the order of about μl/minute.

In a preferred aspect of the invention, to increase sensitivity in a separation system having sub-microliter flow rates, a vented microcapillary column (V-column) is used to vary the rate of flow of sample through the capillary. The first few centimeters of the capillary column preferably are loaded with sample at high flow rates exiting through the vent. After closing the vent (e.g., switching the position of a valve, such as a six-port valve), bound peptides are eluted at much lower flow rates that are compatible with microcapillary separations, such as HPLC (e.g., rates of approximately 300 nl/min).

To maximize separation efficiency, multi-dimensional chromatography can be employed. For example, peptides can be separated in a first dimension by strong cation-exchange (SCX) chromatography. SCX chromatography has the advantage of removing proteases and binding peptides in the presence of accessory molecules that carry no positive charge at pH 3.0, the pH at which peptide elution typically occurs. Thus, peptide binding and elution can occur in the presence of molecules typically used in cellular extraction processes, such as SDS, detergent, urea, DTT, and the like.

At pH 3.0, amine functional groups of peptides almost exclusively contribute to the solution charge state. The nominal charge of any peptide can be determined by adding up the number of lysine, arginine, and histidine residues, with one additional charge contributed by the N-terminus of the peptide. Tryptic peptides generally have solution charge states of 2+ because they terminate in lysine or arginine and have a free N-terminus. A solution charge state of 3+ is seen for tryptic peptides containing one histidine residue. Tryptic peptides carrying a single charge in solution at pH 3.0 are highly specialized, representing either the C-terminal peptide from a polypeptide, an N-terminal peptide that is blocked (e.g., acetylated), or a phosphorylated peptide. Peptides which elute with solution charge states of 4+ or more also represent specialized peptides, e.g., such as disulfide-linked tryptic peptides, missed cleavages, etc. SCX can be used to distinguish among these various charged states.

Other separation methods can be used to complement SCX to achieve additional dimensions of separation. Preferably, such separation methods include, but are not limited to, one or more of: affinity chromatography, liquid chromatography, a gel-based separation method, capillary electrophoresis, reversed phase chromatography, and the like. Preferably, the separation system interfaced with the peptide analyzer is one whose buffering system is compatible with the peptide analyzer being used. For example, when peptides are being evaluated by mass spectrometry, preferably, a separation system which relies on volatile buffers and which does not utilize solutions comprising salts and/or detergents is used. Therefore, in one preferred aspect, the separation system interfaced with the mass spectrometer is a reversed phase liquid chromatography device.

Determining the Mass of Test Peptides

In one aspect, substantially purified test peptides obtained after one or more separation steps are analyzed by a peptide analyzer which evaluates the mass of the peptide or a fragment thereof. Suitable analyzers include, but are not limited to, a mass spectrometer, mass spectrograph, single-focusing mass spectrometer, static field mass spectrometer, dynamic field mass spectrometer, electrostatic analyzer, magnetic analyzer, quadropole analyzer, time of flight analyzer (e.g., a MALDI Quadropole time-of-flight mass spectrometer), Wien analyzer, mass resonant analyzer, double-focusing analyzer, ion cyclotron resonance analyzer, ion trap analyzer, tandem mass spectrometer, liquid secondary ionization MS, and combinations thereof in any order (e.g., as in a multi-analyzer system). Such analyzers are known in the art and are described in, for example, *Mass Spectrometry for the Biological Sciences*, Burlingame and Carr eds., Human Press, Totowa, N.J.).

In general, any analyzer can be used which can separate matter according to its anatomic and molecular mass. Preferably, the peptide analyzer is a tandem MS system (an MS/MS system) since the speed of an MS/MS system enables rapid analysis of low femtomole levels of peptide and can be used to maximize throughput.

In a preferred aspect, the peptide analyzer comprises an ionizing source for generating ions of a test peptide and a detector for detecting the ions generated. The peptide analyzer further comprises a data system for analyzing mass data relating to the ions and for deriving mass data relating to the test peptide.

A sample comprising a test peptide can be delivered to the peptide analyzer using a delivery mechanism as described above. Interfaces between a sample source (e.g., an HPLC column) and ion source can be direct or indirect. For example, there may be an interface that provides for continuous introduction of the sample to the ion source. Alternatively, sample can be intermittently introduced to the ion source (e.g., in response to feedback from the system processor during the separation process, or while the separation system is off-line).

In one aspect, the ion source is an electrospray which is used to provide droplets to the peptide analyzer, each droplet comprising a substantially purified test peptide obtained from previous separation step(s) (e.g., such as HPLC or reversed phase liquid chromatography). During electrospray, a high voltage is applied to a liquid stream causing large droplets to be subdivided into smaller and smaller droplets until a peptide enters the gas phase as an ion. Ionization generally is accomplished when the test peptide loses or gains a proton at one or more basis sites on the peptide (e.g., at the amino terminus, and at lysine and arginine residues). Ionization in electrospray is constant; MALDI can be used to achieve pulsed ionization. Other methods of ionization, include, but are not limited to, plasma desorption ionization, thermospray ionization, and fast atom bombardment ionization as are known in the art.

When MALDI is used, peptides can be delivered to a solid support, e.g., such as a sample plate inserted into the mass spectrometer. The support may comprise a light-absorbent matrix (see, e.g., as described in U.S. Pat. No. 5,288,644). In one aspect, a substantially purified ubiquitinated polypeptide is provided on a sample plate and protease digestion occurs on the sample plate prior to ionization (see, e.g., U.S. Pat. No. 5,827,65). For example, substantially purified ubiquitinated peptides also can be obtained from protease digests as described above and separation by a liquid chromatography method. Preferably, the peptide analyzer further comprises an ion transfer section through which ions are delivered from the ion source to the detector. The ion transfer section comprises an electric and/or magnetic field generator (e.g., an electrode ring) that modulates the acceleration of ions generated by the ionizing source. The electric/magnetic field generator directs ions through the ion transfer section of the peptide analyzer to the ion detector.

Preferably, the peptide analyzer further comprises an ion trap positioned between the ion transfer section of the analyzer and the detector, for performing one or more operations such as ion storage, ion selection and ion collision. The ion trap can be used to fragment ions produced by the ion source (e.g., causing ions to undergo collisional activated dissociation in the presence of a neutral gas ions, such as helium ions). The ion trap also can be used to store ions in stable orbits and to sequentially eject ions based on their mass-to-charge values (m/z) to the detector. An additional separation section can be provided between the ion trap and detector to separate fragments generated in the ion trap (e.g., as in tandem MS). The detector detects the signal strength of each ion (e.g., intensity), which is a reflection of the amount of protonation of the ion.

The peptide analyzer additionally comprises a data system for recording and processing information collected by the detector. The data system can respond to instructions from processor in communication with the separation system and also can provide data to the processor. Preferably, the data system includes one or more of: a computer, an analog to digital conversion module; and control devices for data acquisition, recording, storage and manipulation. More preferably, the device further comprises a mechanism for data reduction, i.e., to transform the initial digital or analog representation of output from the analyzer into a form that is suitable for interpretation, such as a graphical display (e.g., a display of a graph, table of masses, report of abundances of ions, etc.).

The data system can perform various operations such as signal conditioning (e.g., providing instructions to the peptide analyzer to vary voltage, current, and other operating parameters of the peptide analyzer), signal processing, and the like. Data acquisition can be obtained in real time, e.g., at the same time mass data is being generated. However, data acquisition also can be performed after an experiment, e.g., when the mass spectrometer is off line.

The data system can be used to derive a spectrum graph in which relative intensity (i.e., reflecting the amount of protonation of the ion) is plotted against the mass to charge ratio (m/z ratio) of the ion or ion fragment. An average of peaks in a spectrum can be used to obtain the mass of the ion (e.g., peptide) (see, e.g., McLafferty and Turecek, 1993, *Interpretation of Mass Spectra*, University Science Books, CA).

Mass spectra can be searched against a database of reference peptides of known mass and sequence to identify a reference peptide which matches a test peptide (e.g., comprises a mass which is smaller by the amount of mass attributable to a ubiquitin remnant). The database of reference peptides can be generated experimentally, e.g., digesting non-ubiquitinated peptides and analyzing these in the peptide analyzer. The database also can be generated after a virtual digestion process, in which the predicted mass of peptides is generated using a suite of programs such as PROWL (e.g., available from ProteoMetrics, LLC, New York; N.Y.). A number of database search programs exist which can be used to correlate mass spectra of test peptides with amino acid sequences from polypeptide and nucleotide databases, including, but not limited to: the SEQUEST program (Eng, et al., *J. Am. Soc. Mass Spectrom.* 5: 976-89; U.S. Pat. No. 5,538,897; Yates, Jr., III, et al., 1996, *J. Anal. Chem.* 68(17): 534-540A), available from Finnegan Corp., San Jose, Calif.

Data obtained from fragmented peptides can be mapped to a larger peptide or polypeptide sequence by comparing overlapping fragments. Preferably, a ubiquitinated peptide is mapped to the larger polypeptide from which it is derived to identify the ubiquitination site on the polypeptide. Sequence data relating to the larger polypeptide can be obtained from databases known in the art, such as the nonredundant protein database compiled at the Frederick Biomedical Supercomputing Center at Frederick, Md.

In one aspect, the amount and location of ubiquitination is compared to the presence, absence and/or quantity of other types of polypeptide modifications. For example, the presence, absence, and/or quantity of: phosphorylation, sulfation, glycosylation, and/or acetylation can be determined using methods routine in the art (see, e.g., Rossomando, et al., 1992, *Proc. Natl. Acad. Sci. USA* 89: 5779-578; Knight et al., 1993, *Biochemistry* 32: 2031-2035; U.S. Pat. No. 6,271,037). The amount and locations of one or modifications can be correlated with the amount and locations of ubiquitination sites. Preferably, such a determination is made for multiple cell states.

Knowledge of ubiquitination sites can be used to identify compounds that modulate particular ubiquitinated polypeptides (either preventing or enhancing ubiquitination, as appropriate, to normalize the ubiquitination state of the polypeptide). Thus, in one aspect, the method described above may further comprise contacting a first cell with a compound and comparing ubiquitination sites/amounts identified in the first cell with ubiquitination sites/amounts in a second cell not contacted with the compound. Suitable cells that may be tested include, but are not limited to: neurons, cancer cells, immune cells (e.g., T cells), stem cells (embryonic and adult), undifferentiated cells, pluripotent cells, and the like. In one preferred aspect, patterns of ubiquitination are observed in cultured cells, such as P19 cells, pluripotent embryonic carcinoma cells capable of differentiating into cardiac cells and skeletal myocytes upon exposure to DMSO (see, Montross, et al., *J. Cell Sci.* 113 (Pt. 10): 1759-70).

Compounds which can be evaluated include, but are not limited to: drugs; toxins; proteins; polypeptides; peptides; amino acids; antigens; cells, cell nuclei, organelles, portions of cell membranes; viruses; receptors; modulators of receptors (e.g., agonists, antagonists, and the like); enzymes; enzyme modulators (e.g., such as inhibitors, cofactors, and the like); enzyme substrates; hormones; nucleic acids (e.g., such as oligonucleotides; polynucleotides; genes, cDNAs; RNA; antisense molecules, ribozymes, aptamers), and combinations thereof. Compounds also can be obtained from synthetic libraries from drug companies and other commercially available sources known in the art (e.g., including, but not limited, to the LeadQuest® library) or can be generated through combinatorial synthesis using methods well known in the art. A compound is identified as a modulating agent if it alters the site of ubiquitination of a polypeptide and/or if it alters the amount of ubiquitination by an amount that is significantly different from the amount observed in a control cell (e.g., not treated with compound) (setting p values to <0.05).

Compounds identified as modulating agents are used in methods of treatment of pathologies associated with abnormal sites/levels of ubiquitination. For administration to a patient, one or more such compounds are generally formulated as a pharmaceutical composition. Preferably, a pharmaceutical composition is a sterile aqueous or non-aqueous solution, suspension or emulsion, which additionally comprises a physiologically acceptable carrier (i.e., a non-toxic material that does not interfere with the activity of the active ingredient). More preferably, the composition also is non-pyrogenic and free of viruses or other microorganisms. Any suitable carrier known to those of ordinary skill in the art may be used. Representative carriers include, but are not limited to: physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Routes and frequency of administration, as well doses, will vary from patient to patient. In general, the pharmaceutical compositions is administered intravenously, intraperitoneally, intramuscularly, subcutaneously, intracavity or transdermally. Between 1 and 6 doses is administered daily. A suitable dose is an amount that is sufficient to show improvement in the symptoms of a patient afflicted with a disease associated an aberrant ubiquitination state. Such improvement may be detected by monitoring appropriate clinical or biochemical endpoints as is known in the art. In general, the amount of modulating agent present in a dose, or produced in situ by DNA present in a dose (e.g., where the modulating agent is a polypeptide or peptide encoded by the DNA), ranges from about 1 µg to about 100 mg per kg of host. Suitable dose sizes will vary with the size of the patient, but will typically range from about 10 mL to about 500 mL for 10-60 kg animal. A patient can be a mammal, such as a human, or a domestic animal.

In another aspect, the ubiquitination states (e.g., sites and amount of ubiquitination) of first and second cells are evaluated. Preferably, the second cell differs from the first cell in expressing one or more recombinant DNA molecules, but is otherwise genetically identical to the first cell. Alternatively, or additionally, the second cell can comprise mutations or variant allelic forms of one or more genes. In one aspect, DNA molecules encoding regulators of the ubiquitin pathway can be introduced into the second cell (e.g., E1, E2, E3, deubiquitinating proteins, fragments thereof, mutant forms thereof, variants, and modified forms thereof, or compounds identified as above) and alterations in the ubiquitination state in the second cell can be determined. DNA molecules can be introduced into the cell using methods routine in the art, including, but not limited to: transfection, transformation, electroporation, electrofusion, microinjection, and germline transfer.

Computer Systems and Databases

The invention also provides methods for generating a database comprising data files for storing information relating to diagnostic peptide fragmentation signatures. Preferably, data in the data files include one or more peptide fragmentation signatures characteristic or diagnostic of a cell state (e.g., such as a state which is characteristic of a disease, a normal physiological response, a developmental process, exposure to a therapeutic agent, exposure to a toxic agent or a potentially toxic agent, and/or exposure to a condition). Data in the data files also preferably includes values corresponding to level of proteins corresponding to the peptide fragmentation signatures found in a particular cell state.

In one aspect, for a cell state determined by the differential expression of at least one protein, a data file corresponding to the cell state will minimally comprise data relating to the mass spectra observed after peptide fragmentation of a peptide internal standard diagnostic of the protein. Preferably, the data file will include a value corresponding to the level of the protein in a cell having the cell state. For example, a tumor cell state is associated with the overexpression of p53 (see, e.g., Kern, et al., 2001, *Int. J. Oncol.* 21(2): 243-9). The data file will comprise mass spectral data observed after fragmentation of a labeled peptide internal standard corresponding to a subsequence of p53. Preferably, the data file also comprises a value relating to the level of p53 in a tumor cell. The value may be expressed as a relative value (e.g., a ratio of the level of p53 in the tumor cell to the level of p53 in a normal cell) or as an absolute value (e.g., expressed in nM or as a % of total cellular proteins).

Preferably, the data files also include information relating to the presence or amount of a modified form of a target a polypeptide in at least one cell and to mass spectral data diagnostic of the modified form (i.e., peak data for a fragmented peptide internal standard which corresponds to the modified form). More preferably, the data files also comprise spectral data diagnostic of the unmodified form as well as data corresponding to the level of the unmodified form.

Thus, in one aspect, data relating to ubiquitination sites and amounts of ubiquitination are stored in a database to create a proteome map of ubiquitinated proteins. Preferably, the database comprises a collection of data files relating to all ubiquitinated polypeptides in a particular cell type. The database preferably further comprises data relating to the origin of the cell, e.g., such as data relating to a patient from whom a cell was obtained. More preferably, the database comprises data relating to cells obtained from a plurality of patients. In one aspect, the database comprises data relating to the ubiquitination of a plurality of different cell types (e.g., cells from patients with a pathology, normal patients, cells at various stages of differentiation, and the like). In another aspect, data relating to ubiquitination patterns in cells obtained from patients comprising a neurological disease are stored in the database. For example, information relating to ubiquitination in cell samples from patients having any of Alzheimer's disease; amyotrophic lateral sclerosis; dementia, depression; Down's syndrome; Huntington's disease; peripheral neuropathy; multiple sclerosis; neurofibromatosis; Parkinson's disease; and schizophrenia, can be included in the database.

In a further aspect, data relating to ubiquitination patterns in cells from patients with cancer are stored in the database, including, but not limited to patients with: adenocarcinoma; leukemia; lymphoma; melanoma; myeloma; sarcoma; teratocarcinoma; and, in particular, cancers of the adrenal gland; bladder; bone; bone marrow; brain; breast; cervix; gall bladder; ganglia; gastrointestinal tract; heart; kidney; liver; lung; muscle; ovary; pancreas; parathyroid; prostate; salivary glands; skin; spleen; testis; thymus; thyroid; and uterus.

Additionally, data of ubiquitination patterns in cells from patients with an immune disorder may be included in the database. Such a disorder can include: acquired immunodeficiency syndrome (AIDS); Addison's disease; adult respiratory distress syndrome; allergies; ankylosing spondylitis; amyloidosis; anemia; asthma; atherosclerosis; autoimmune hemolytic anemia; autoimmune thyroiditis; bronchitis; cholecystitis; contact dermatitis; Crohn's disease; atopic dermatitis; dermatomyositis; diabetes mellitus; emphysema; episodic lymphopenia with lymphocytotoxins; erythroblastosis fetalis; erythema nodosum; atrophic gastritis; glomerulonephritis; Goodpasture's syndrome; gout; Graves' disease; Hashimoto's thyroiditis; hypereosinophilia; irritable bowel syndrome; myasthenia gravis; myocardial or pericardial inflammation; osteoarthritis; osteoporosis; pancreatitis; polymyositis; psoriasis; Reiter's syndrome; rheumatoid arthritis; scleroderma; Sjogren's syndrome; systemic anaphylaxis; systemic lupus erythematosus; systemic sclerosis; thrombocytopenic purpura; ulcerative colitis; uveitis; Werner syndrome; and viral, bacterial, fungal, parasitic, protozoal, and helminthic infections.

Data regarding ubiquitination in apoptotic cells and in pathologies associated with the misregulation of apoptosis also can be obtained using methods according to the invention.

In a further aspect, data regarding ubiquitination in cardiac cells and cells from patients exhibiting a cardiac disease or at risk for a cardiac disease are obtained. In one aspect, the disease is an infarction or a condition relating to ischemia. In another aspect, the disease is cardiomyopathy.

In still a further aspect, data is obtained from cells obtained from a patient comprising a chromosomal deletion or mutation of nucleic acids encoding one or more polypeptides involved in the ubiquitination process. In one aspect, the patient comprises a 22q11.2 deletion.

It should be obvious to those of skill in the art, that the invention may be used to characterize a large number of pathologies associated with ubiquitin degradation and that the above examples are not intended to be limiting.

Differences in ubiquitination patterns (sites and/or quantity of ubiquitination) in cells with different cell states can be used to identify diagnostic markers for a cell state. Thus, in one aspect, ubiquitination at a particular polypeptide site is associated with disease or risk of developing a disease (e.g., a statistically significant chance of having or developing the disease). Correlations between a particular state of ubiquitination and a disease can be identified using the database described above and suitable statistical programs, expert systems, and/or data mining systems, as are known in the art, for identifying relationships between records in data files (e.g., such as records relating to ubiquitination patterns and records relating to patients from whom cells were derived). In one aspect, the ubiquitination state of a cell is determined and used to determine the presence or risk of a pathology, such as a neurological disease, cancer, or an immune disease (i.e., any of the diseases described above). Molecular probes can be developed based on this information (e.g., antibodies which recognize a polypeptide ubiquitinated at the site but not a polypeptide which is not ubiquitinated at the site) and can be used in screening assays to identify patients have a disease or who are at risk of developing a disease.

In one aspect, the database also comprises data relating to the source of a cell whose cell state is being evaluated. For example, the database comprises data relating to identifying characteristics of a patient from whom the cell is derived.

The invention further provides a computer memory comprising data files for storing information relating to the diagnostic fragmentation signatures of peptide internal standards. In one preferred aspect, the database comprises peptide diagnostic signatures, e.g., mass spectral data obtained after fragmentation of one or more peptide internal standards, which can be used to identify a cell having a particular cell state. More preferably, the database includes data relating to a plurality of cell state profiles, i.e., data relating to levels of target proteins identified by the peptide internal standards in a plurality of cells having different cell states. For example, profiles of disease states may be included in the database and these profiles will include measurements of levels of one or more proteins, or modified forms thereof, characteristic of the disease state. Profiles of cells exposed to different compounds include measurements of levels of proteins or modified forms thereof characteristic of the response(s) of the cells to the compounds. In one aspect, the measurements are obtained by performing any of the methods described above.

Preferably, the database is in electronic form and the cell state profiles, which are also in electronic form, provide measurements of levels of a plurality of proteins in a cell or cells of one or more subjects. In one aspect, the database comprises measurements of more than about 5, more than about 10, more than about 30, more than about 50, more than about 100, more than about 500, more than about 1000, more than about 10,000, or more than about 100,000 proteins in a cell, i.e., the database comprises data relating to the proteome of a cell. The measurements represent levels of modified and/or unmodified forms of the proteins. In one aspect, the measurements also include data regarding the site of protein modifications in one or more proteins in a cell.

In one preferred aspect, cell state profiles comprise quantitative data relating to target proteins and/or modified forms thereof obtained by using one or more of the methods described above.

A variety of data storage structures are available for creating a computer readable medium or memory comprising data files of the database. The choice of the data storage structure will generally be based on the means chosen to access the stored information. For example, the data can be stored in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text files, pdf files, or database structures) in order to obtain computer readable medium or a memory having recorded thereon data relating to diagnostic fragmentation signatures, e.g., such as mass spectral data obtained after fragmentation of the peptide internal standards, and protein levels and/or data relating to the presence and quantity of modified proteins (e.g., such as ubiquitinated proteins) in a sample.

Correlations between a particular diagnostic signature observed and a cell state (e.g., a disease, genotype, tissue type, etc.) may be known or may be identified using the database described above and suitable statistical programs, expert systems, and/or data mining systems, as are known in the art. In one aspect, the diagnostic signature is provided by a diagnostic pattern of protein modification, such as protein ubiquitination.

In another aspect, the invention provides a computer system comprising: a database having data files containing information identifying diagnostic fragmentation signatures (e.g., mass spectral peaks) as corresponding to particular peptide internal standards which in turn are identified as corresponding to particular target proteins. Preferably, the data files also comprise information for relating the diagnostic fragmentation signatures so identified to one or more cell states, e.g., where the target protein corresponding to the peptide internal standard is diagnostic of a cell state, the peptide internal standard and fragmentation signature are also identified within the data file as being diagnostic of a cell state. In one preferred aspect, the system further comprises a user interface allowing a user to selectively view information relating to a diagnostic fragmentation signature and to obtain information about a cell state. The interface may comprise links allowing a user to access different portions of the database by selecting the links (e.g. by moving a cursor to the link and clicking a mouse or by using a keystroke on a keypad). The interface may additionally display fields for entering information relating to a sample being evaluated.

Still more preferably, the system is capable of comparing diagnostic fragmentation signatures of known peptide internal standards to mass spectral data obtained for peptides in a sample spiked with one or more internal standards in order to determine and/or quantify levels of target proteins corresponding to the standards in the sample. When a match is identified, the system may also provide information regarding the cell state for which the peptide internal standard is diagnostic (i.e., the system will identify the source of the cell, the compound to which a cell has been exposed, and/or a disease which the cell is responding to). In some aspects, sets of peptide internal standards are evaluated, as only the set will be diagnostic.

The system may also be used to collect and categorize peptide fragmentation signatures for different types of cell states to identify sets of peptide internal standards characteristic of particular cell states. In this aspect, preferably, the system comprises a relational database. More preferably, the system further comprises an expert system for identifying sets of peptide internal standards that are diagnostic of different cell states. In one aspect, the system is capable of clustering related information. Suitable clustering programs are known in the art and are described in, for example, U.S. Pat. No. 6,303,297.

The system preferably comprises a means for linking a database comprising data files of diagnostic fragmentation signatures to other databases, e.g., such as genomic databases, pharmacological databases, patient databases, proteomic databases, and the like.

Preferably, the system comprises in combination, a data entry means, a display means (e.g., graphic user interface); a programmable central processing unit; and a data storage means comprising the data files and information described above, electronically stored in a relational database.

Preferably, the central processing unit comprises an operating system for managing a computer and its network interconnections. This operating system can be, for example, of the Microsoft Windows' family, such as Windows 95, Windows 98, or Windows NT, or any new Windows programmed developed. A software component representing common languages may be provided. Preferred languages include C/C++, and JAVA®. In one aspect, methods of this invention are programmed in software packages which allow symbolic entry of equations, high-level specification of processing, and statistical evaluations.

Reagents and Kits

Reagents and Kits Comprising Peptide Internal Standards

The invention further provides reagents useful for performing the method. In one aspect, a reagent according to the invention comprises a peptide internal standard labeled with a stable isotope. Preferably, the standard has a unique peptide fragmentation signature diagnostic of the peptide. The peptide is a subsequence of a known protein and can be used to identify the presence of and/or quantify the protein in sample, such as a cell lysate.

The invention additionally provides kits comprising one or more peptide internal standards labeled with a stable isotope or reagents suitable for performing such labeling. In certain preferred embodiments, the method utilizes isotopes of hydrogen, nitrogen, oxygen, carbon, or sulfur. Suitable isotopes include, but are not limited to, $^{2}H$, $^{13}C$, $^{15}N$, $^{17}O$, $^{18}O$, or $^{34}S$. In another aspect, pairs of peptide internal standards are provided, comprising identical peptide portions but distinguishable labels, e.g., peptides may be labeled at multiple sites to provide different heavy forms of the peptide. Pairs of peptide internal standards corresponding to modified and unmodified peptides also can be provided.

In one aspect, a kit comprises peptide internal standards comprising different peptide subsequences from a single known protein. In another aspect, the kit comprises peptide internal standards corresponding to different known or predicted modified forms of a polypeptide. In a further aspect, the kit comprises peptide internal standards corresponding to sets of related proteins, e.g., such as proteins involved in a molecular pathway (a signal transduction pathway, a cell cycle, etc), or which are diagnostic of particular disease states, developmental stages, tissue types, genotypes, etc.

Peptide internal standards corresponding to a set may be provided in separate containers or as a mixture or "cocktail" of peptide internal standards.

In one aspect, a plurality of peptide internal standards representing a MAPK signal transduction pathway is provided. Preferably, the kit comprises at least two, at least about 5, at least about 10 or more, of peptide internal standards corresponding to any of MAPK, GRB2, mSOS, ras, raf, MEK, p85, KHS1, GCK1, HPK1, MEKK 1-5, ELK1, c-JUN, ATF-2, 3APK, MLK1-4, PAK, MKK, p38, a SAPK subunit, hsp27, and one or more inflammatory cytokines.

In another aspect, a set of peptide internal standards is provided which comprises at least about two, at least about 5 or more, of peptide internal standards which correspond to proteins selected from the group including, but not limited to, PLC isoenzymes, phosphatidylinositol 3-kinase (PI-3 kinase), an actin-binding protein, a phospholipase D isoform, (PLD), and receptor and nonreceptor PTKs.

In another aspect, a set of peptide internal standards is provided which comprises at least about 2, at least about 5, or more, of peptide internal standards which correspond to proteins involved in a JAK signaling pathway, e.g., such as one or more of JAK 1-3, a STAT protein, IL-2, TYK2, CD4, IL-4, CD45, a type I interferon (IFN) receptor complex protein, an IFN subunit, and the like.

In a further aspect, a set of peptide internal standards is provided which comprises at least about 2, at least about 5, or more of peptide internal standards which correspond to cytokines. Preferably, such a set comprises standards selected from the group including, but not limited to, pro- and anti-inflammatory cytokines (which may each comprise their own set or which may be provided as a mixed set of peptide internal standards).

In still another aspect, a set of peptide internal standards is provided which comprises a peptide diagnostic of a cellular differentiation antigen or CD. Such kits are useful for tissue typing.

In one aspect, peptides corresponding to known variants or mutations in a target polypeptide, or which are randomly varied to identify all possible mutations in an amino acid sequence, are provided in the kit. In a preferred aspect, peptide internal standards corresponding to proteins expressed from nucleic acids comprising single nucleotide polymorphisms are provided.

Peptide internal standards may include peptides corresponding to variant proteins selected from the group consisting of BRCA1; BRCA2; CFTR; p53; a JAK protein; a STAT protein; blood group antigens; HLA proteins; MHC proteins; G-Protein Coupled Receptors; apolipoprotein E; kinases (e.g., such as hCds1, MTKs, PTK, CDKs, STKs, CaMs, and the like) (see, e.g., U.S. Pat. No. 6,426,206); phosphatases; human drug metabolizing proteins; viral proteins, including but not limited to viral envelope proteins (e.g., an HIV envelope protein); transporter proteins; and the like.

In one aspect, the peptide internal standard comprises a label associated with a modified amino acid residue, such as a phosphorylated amino acid residue, a glycosylated amino acid residue, an acetylated amino acid residue, a farnesylated residue, a ribosylated residue, and the like. In another aspect, a pair of reagents is provided, a peptide internal standard corresponding to a modified peptide and a peptide internal standard corresponding to a peptide, identical in sequence but not modified.

In another aspect, one or more control peptide internal standards are provided. For example, a positive control may be a peptide internal standard corresponding to a constitutively expressed protein, while a negative peptide internal standard may be provided corresponding to a protein known not to be expressed in a particular cell or species being evaluated. For example, in a kit comprising peptide internal standards for evaluating a cell state in a human being, a plant peptide internal standard may be provided.

In still another aspect, a kit comprises a labeled peptide internal standard as described above and software for analyzing mass spectra (e.g., such as SEQUEST).

Preferably, the kit also comprises a means for providing access to a computer memory comprising data files storing information relating to the diagnostic fragmentation signatures of one or more peptide internal standards. Access may be in the form of a computer readable program product comprising the memory, or in the form of a URL and/or password for accessing an internet site for connecting a user to such a memory. In another aspect, the kit comprises diagnostic fragmentation signatures (e.g., such as mass spectral data) in electronic or written form, and/or comprises data, in electronic or written form, relating to amounts of target proteins characteristic of one or more different cell states and corresponding to peptides which produce the fragmentation signatures.

The kit may further comprise expression analysis software on computer readable medium, which is capable of being encoded in a memory of a computer having a processor and capable of causing the processor to perform a method comprising: determining a test cell state profile from peptide fragmentation patterns in a test sample comprising a cell with an unknown cell state or a cell state being verified; receiving a diagnostic profile characteristic of a known cell state; and comparing the test cell state profile with the diagnostic profile.

In one aspect, the test cell state profile comprises values of levels of peptides in a test sample that correspond to one or more peptide internal standards provided in the kit. The diagnostic profile comprises measured levels of the one or more peptides in a sample having the known cell state (e.g., a cell state corresponding to a normal physiological response or to an abnormal physiological response, such as a disease).

Preferably, the software enables a processor to receive a plurality of diagnostic profiles and to select a diagnostic profile that most closely resembles or "matches" the profile obtained for the test cell state profile by matching values of levels of proteins determined in the test sample to values in a diagnostic profile, to identify substantially all of a diagnostic profile which matches the test cell state profile.

Substantially all of a diagnostic profile is matched by a test cell state profile when most of the cellular constituents (e.g., proteins in the proteome) which are diagnostic of the cell state, are found to have substantially the same value in the two profiles within a margin provided by experimental error. Preferably, at least about 75% of the diagnostic proteins can be matched, at least about 80%, at least about 85%, at least about 90% or at least about 95% can be matched. Preferably, where one, or only a few proteins (e.g., less than 10) are used to establish s diagnostic profile, preferably all of the proteins have substantially the same value.

Kits For Detecting Protein Ubiquitination

The invention further provides a kit for detecting and/or quantifying a protein modification, such as ubiquitination. In one aspect, the kit comprises a ubiquitin binding molecule (e.g., an antibody, an affinity molecule for recognizing a tag coupled to a ubiquitin molecule, and the like), and one or more components, including, but not limited to: a protease (e.g., such as trypsin); a ubiquitinated molecule comprising known ubiquitination sites; acetonitrile; silica resin; heptafluorobutyric acid; urea (e.g., 8M urea); an isotope-coded affinity tag (e.g., such as an ICAT label or pair of ICAT labels) (see, Gygi and Rist., 1999, *Nat. Biotechnol.* 17: 994-999; U.S. Provisional Application No. 60/305,808, filed Jul. 16, 2001) or an affinity tag coupleable to an isotope; a mass modifying moiety; a sample plate for use with a mass spectrometer; a light-absorbent matrix; an ion exchange resin; software for analyzing mass spectra (e.g., such as SEQUEST); fused silica capillary tubing; and access to a computer memory comprising data files storing information relating to ubiquitination sites for a plurality of polypeptides for a plurality of different cells. Access may be in the form of a computer readable program product comprising the memory, or in the form of a URL and/or password for accessing an internet site for connecting a user to such a memory. In one preferred aspect, an isotope-labeled peptide comprising Gly-Gly residues and known peptide amino acid sequences is provided as an internal standard. In still a further aspect, an isotope-labeled Gly-Gly dipeptide is provided.

In one particularly preferred aspect, a kit is provided which comprises an antibody that specifically recognizes a peptide product of a protease-digested ubiquitinated protein which comprises a ubiquitin remnant. Preferably, the antibody does not recognize the same peptide when it does not comprise the ubiquitin remnant. Methods of making antibodies which are specific for modified forms of peptides are routine in the art.

More preferably, the kit comprises one or more antibodies which specifically recognize peptides produced by protease digestion of ubiquitinated forms of ubiquitin. In one aspect, at least one antibody in the kit specifically recognizes a peptide comprising any of the $K^{48}$, $K^{63}$, $K^{11}$, $K^{27}$, $K^{6}$, $K^{29}$, and $K^{33}$ sites of the ubiquitin polypeptide modified by a ubiquitin remnant at that site. In another aspect, an antibody is provided which specifically recognize a ubiquitin polypeptide ubiquitinated at one or more of the $K^{48}$, $K^{63}$, $K^{11}$, $K^{27}$, $K^{6}$, $K^{29}$, and $K^{33}$ sites. Either type of antibody can be used to evaluate the site specificity and amount of ubiquitination at one or more sites on a ubiquitin polypeptide, e.g., to diagnose a pathology or stage of differentiation associated with a particular pattern of ubiquitination. Preferably, these antibodies do not recognize forms of ubiquitin not ubiquitinated at the site of interest (although such antibodies also may be included in the kits of the invention as controls).

Diagnosis may be performed by using the peptide-specific antibodies (which may also be polypeptide-specific antibodies) or the polypeptide-specific antibodies (which may also be peptide-specific antibodies) or a combination thereof. In one aspect, however, a sample is digested by a protease (e.g., such as trypsin) and one or more of the antibodies specific for a peptide comprising a ubiquitin remnant at a particular site is used to determine whether the sample is reactive with the antibody, e.g., by performing a standard immunoassay. Thus, reagents useful for conducting immunoassays also may be included in the kits. The presence and level of reactivity of the antibodies can be used to monitor the site specificity and amount of ubiquitination.

Panels of antibodies can be used simultaneously to perform the analysis (e.g., by using antibodies comprising distinguishable labels). Panels of antibodies also can be used in parallel or in sequential assays. Therefore, in one preferred aspect, a kit according to the invention comprises a panel of antibodies comprising antibodies specific for ubiquitinated peptides/polypeptides ubiquitinated at one or more of the $K^{48}$, $K^{63}$, $K^{11}$, $K^{27}$, $K^{6}$, $K^{29}$, and $K^{33}$ Sites.

The presence, absence, level, and/or site-specificity of other types of modifications, such as phosphorylation, also can be determined along with the presence, absence, level and/or site specificity of ubiquitination. For example, in addition to identifying the presence and/or amount of ubiquitination at the $K^{48}$, $K^{63}$, $K^{11}$, $K^{27}$, $K^{6}$, $K^{29}$, and $K^{33}$ sites of ubiquitin, the presence and/or absence of phosphorylation at particular phosphorylation sites on the ubiquitin polypeptide also can be determined. Phosphorylation can be determined by using mass spectrometry or through the use of antibodies specific to particular phosphorylated forms of ubiquitin polypeptides or peptides. In one preferred aspect, the kit according to the invention further comprises an antibody specific for a phosphorylated form of a ubiquitin polypeptide or peptide and which does not recognize the non-phosphorylated form. More preferably, the kit comprises an antibody which recognizes a ubiquitin polypeptide or peptide phosphorylated at $Ser^{57}$ and which does not recognize polypeptides/peptides which are not phosphorylated at this site.

EXAMPLE

The invention will now be further illustrated with reference to the following example. It will be appreciated that what follows is by way of example only and that modifications to detail may be made while still falling within the scope of the invention.

Example 1

Preparation of Ubiquitin-Conjugates from *S. cerevisiae*

Figure 8:
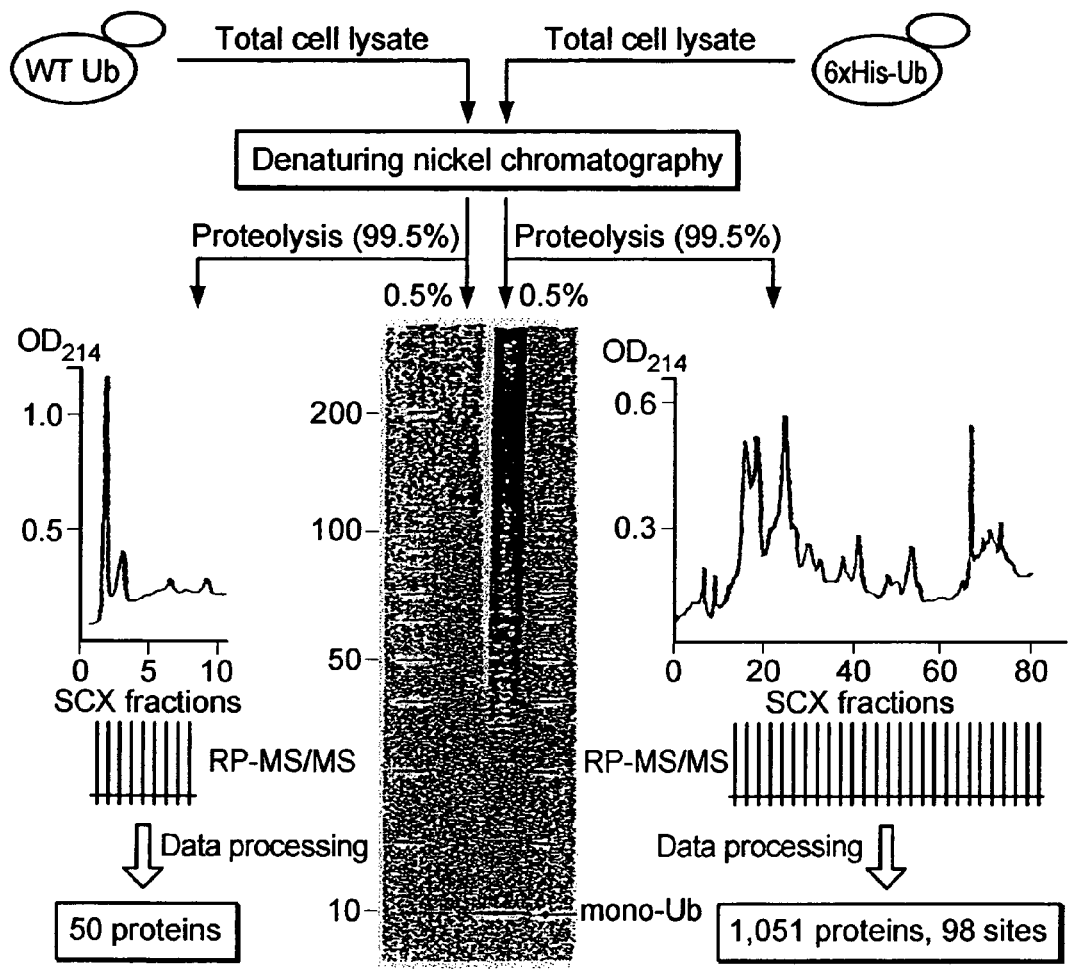
FIG. 8 is a schematic showing the isolation and sequence analysis of yeast ubiquitin-conjugates according to one aspect of the invention.

Isolation and identification of yeast ubiquitin-conjugates was accomplished as illustrated in FIG. 8. 100 mg of whole yeast lysates were harvested from cells growing through log phase (OD610 1-1.5) from two strains of yeast differing in the expression of 6×His-tagged ubiquitin. Strain SUB592 (JSY171), expressing tagged ubiquitin, and control strain, SUB280 (Spence, et al., 2000, *Cell* 102: 67-76), were grown to log phase and lysed in buffer A (10 mM Tris, pH 8.0, 0.2 M $NaH_2PO_4$, 8M Urea) using glass beads. A $Ni^{2+}$-NTA-agarose column (Qiagen, Chatsworth, Calif.) was loaded with the clarified lysates, sequentially washed with 30 volumes (bed volume) of buffer A twice, 3 volumes of buffer B (10 mM Tris, pH 6.3, 0.1 M $NaH_2PO_4$, 8M Urea), and eluted with 3 volumes of buffer C (10 mM Tris, pH 4.5, 0.1 M $NaH_2PO_4$, 8M Urea). A portion (0.5%) of eluted polypeptides was examined by SDS-PAGE and silver staining. The remaining polypeptides (99.5%) were reduced, alkylated at cysteinyl residues, and proteolyzed with trypsin to generate test peptides.

Two-Dimensional Liquid Chromatography with Tandem Mass Spectrometry

Because the resulting peptide mixture was enormously complex, it was separated by two dimensions of chromatography to allow thousands of peptides to be sequenced. The tryptic peptides were separated in the first dimension by strong cation exchange (SCX) chromatography with fraction collection every minute, followed by nano-scale microcapillary reverse-phase (RP) chromatography. Peptides of the control strain were eluted in a 10-minute gradient from 0% to 100% solvent B. Ubiquitin-conjugated peptides were fractionated in a 70-minute gradient from 5% to 30% solvent B. All collected fractions (80) were reduced in volume and then analyzed individually using 75 µm i.d.×12 cm self-packed fused silica C18 capillary columns.

Peptides were eluted for each analysis during a 90-minute gradient in which the eluted peptide ions were detected, isolated, and fragmented in a completely automated fashion on an LCQ-DECA ion trap mass spectrometer (Thermo Finnigan, San Jose, Calif.). During elution, peptides ions were constantly detected and selected for sequencing in an automated fashion with one peptide being sequenced on average every 2 seconds. More than 96,000 sequencing attempts were acquired for ubiquitin-conjugates during the entire experiment.

Data Processing

All MS/MS spectra were searched against the yeast ORF's database supplemented with the sequence of the recombinant 6×His myc-ubiquitin using the SEQUEST algorithm (Eng, et al. 1994, supra). Modifications were permitted to allow for the detection of the following (mass shift shown in Daltons); oxidized methionines (+16), carboxymethylated cysteine (+57), ubiquitinated lysine (+114), and phosphorylated serine, threonine, tyrosine (+80). SEQUEST criteria were as described in Washburn, et al, 2001, *Nat. Biotechnol.* 19: 242-7, and further included: (i) an Xcorr of greater than 2.0, 2.2, and 3.75 for 1+, 2+, and 3+, charge state peptides, respectively; ii) the requirement that a peptide must be partially or fully tryptic; and (iii) the requirement that a peptide must have a fCn score of >0.1. Peptides were also were manually verified from each polypeptide identified by two or less qualifying peptides.

Identification of 1,051 Ubiquitin Conjugated Candidates.

Database searching with SEQUEST identified 12,922 peptides using the acceptance criteria described above. After removing redundancy, 5,424 unique peptides were identified, corresponding to 1,237 polypeptides. These polypeptides were further filtered by: (i) removing 48 polypeptides detected in the control fraction; (ii) removing 34 polypeptides which contained 3 or more consecutive histidine residues; (iii) removing 104 polypeptides considered to be highly abundant (codon bias greater than 0.35 and identified by less than three peptides); and (iv) accepting 70 polypeptides for which the precise ubiquitination site was found. This filtering resulted in final acceptance of 1,051 polypeptides as candidate targets of ubiquitination.

Figure 9A:
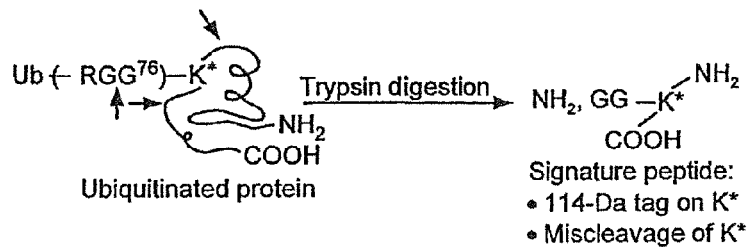
FIGS. 9A-C illustrate a strategy for identifying a site of ubiquitination by tandem mass spectrometry according to one aspect of the invention.
Figure 9B:
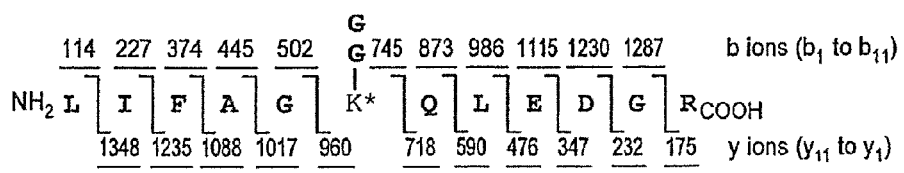
Figure 9C:
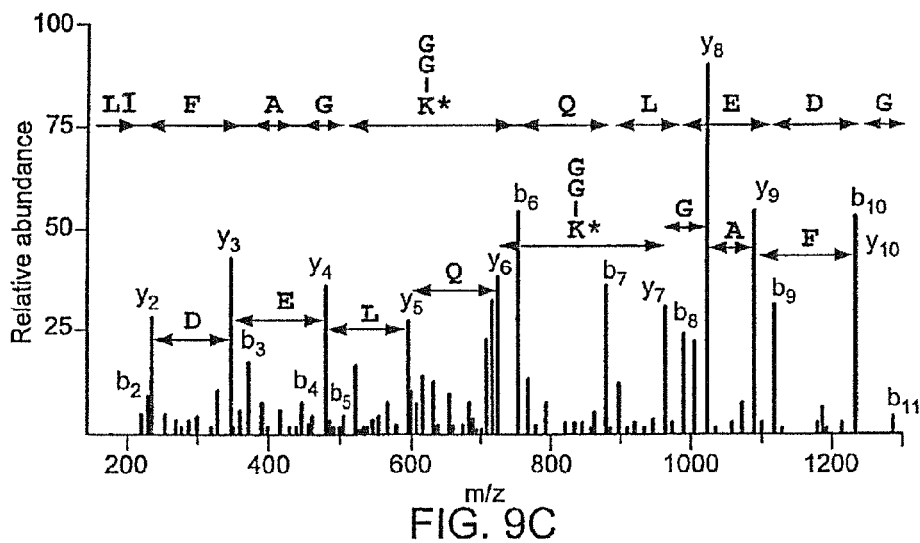

In addition to unambiguously identifying more than 1,000 candidates for ubiquitin conjugation, the precise site of ubiquitination was identified for a number of polypeptides. As shown in FIGS. 9A-C, using mass differences characteristic of ubiquitin remnants of the protease digestion process, a peptide (a ubiquitin peptide, in this example) comprising a site of ubiquitination could be identified. For example, where trypsin is used as the protease, a 114 dalton mass change can be observed due to a Gly-Gly residue linked to a lysine in the peptide through an isopeptide bond. A missed cleavage site also is observed where ubiquitination has occurred. As can be shown in FIGS. 10A-C, this approach identified polypeptides comprising multiple ubiquitination sites, including ubiquitin itself. Methods of utilizing the SEQUEST algorithm to detect modified peptide are described in Jaffe, et al., 1998, *Biochemistry* 37(46): 16211-24, for example.

The types and classes of ubiquitinated polypeptides identified were compared to the entire yeast proteome. Codon bias is a measure of the propensity of a gene to utilize only a subset of the 61 potential codons to produce its amino acids (Bennetzen, et al., 1982, *J. Biol. Chem.* 257: 3026-31, 1982) and has been shown to be a good indicator of polypeptide expression levels under specific growth conditions (Futcher, et al., 1999, *Mol. Cell. Biol.* 19: 7357-68). As a general rule, a codon bias value of less than 0.1 would reflect medium to highly abundant polypeptides. More than one-half of the genes in yeast (57%) have codon bias values less than 0.1 and are thus thought to be expressed at low abundance. A majority of ubiquitinated polypeptides are highly enriched for low abundance proteins, such as regulatory proteins.

Figure 11A:
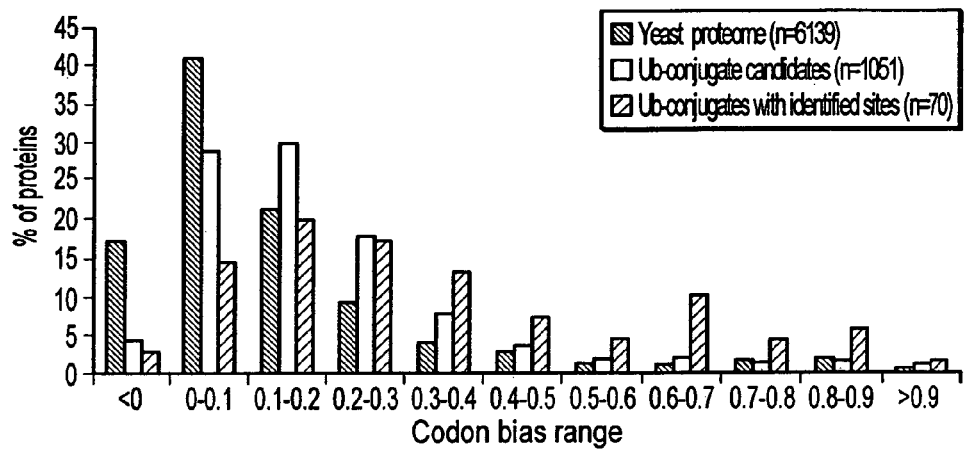
FIGS. 11A-C show comparisons of protein expression, protein environment and function in the yeast proteome characterized using methods according to the invention.
Figure 11B:
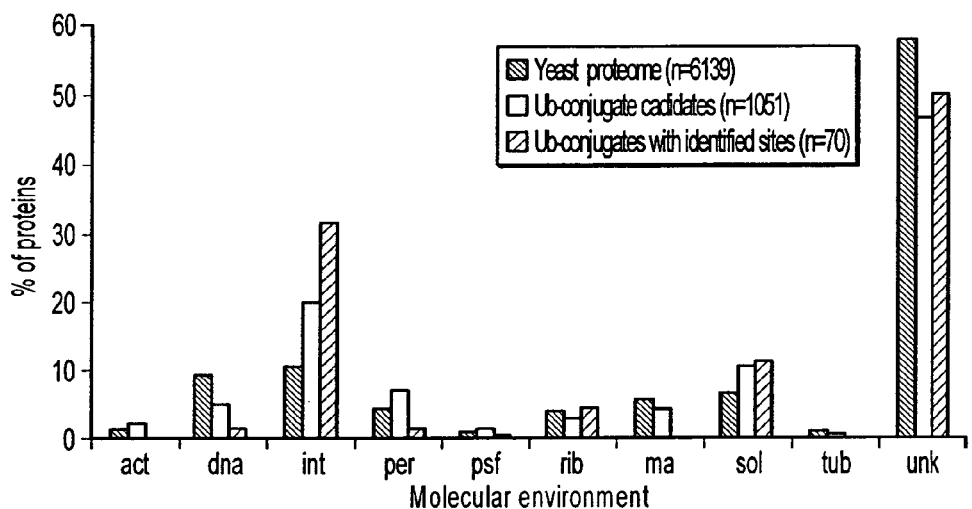
Figure 11C:
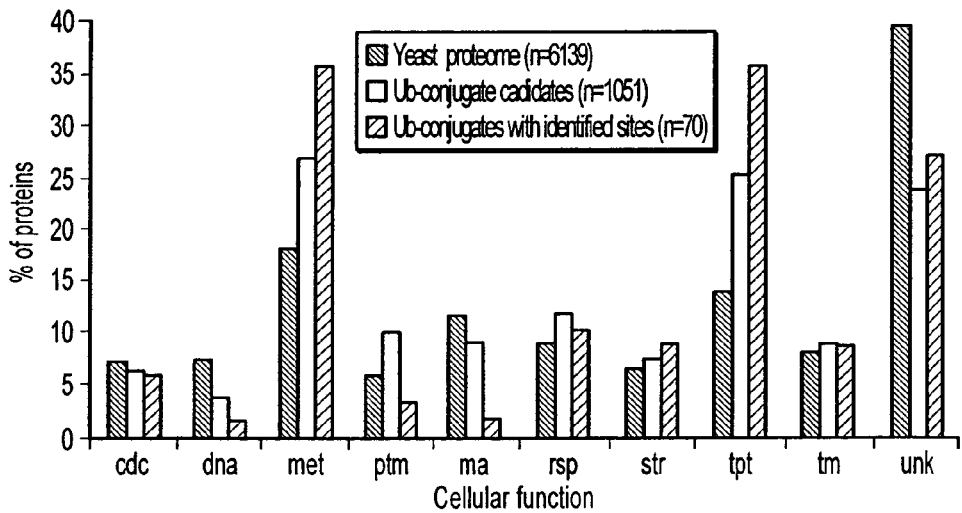

The molecular environment of the polypeptides detected is shown in FIG. 11B. Of the sites detected, more than one-third were attributable to integral membrane polypeptides, supporting prior studies that have indicating that downregulation of some membrane polypeptides requires modification by ubiquitin for their internalization and degradation in lysosmes/vacuoles (see, e.g., Hicke, 1999, *Trends Cell Biol.* 9: 107-112). The cellular function of the polypeptides identified was compared against the yeast proteome (see, e.g., FIG. 11C). Polypeptides from every category of cellular polypeptide were detected.

Polypeptides involved in metabolism and transport were detected with the highest frequencies.

Ubiquitination sites for 70 polypeptides were identified and 98 sites were found. Of these sites, 17 were attributable to the ubiquitination of ubiquitin itself. The qualitative abundance of ubiquitination at different sites on the ubiquitin molecule could be assessed based on the number of fractions in which the peptide occurred, the magnitude of the peptide ion as measured by mass spectrometry, and the number of times the peptide was independently identified by the database searching software. The relative abundance of different ubiquitinated forms was determined to be $K^{48}$>$K^{63}$>$K^{11}$>>$K^{27}$ and $K^6$ (e.g., see FIG. 10B). The $K^{11}$, $K^{27}$, and $K^6$ sites were newly identified by the method according to the invention. The $K^{63}$ site has been implicated in processes other than degradation (e.g., DNA repair, endocytosis, etc.) (see, e.g., Finley, 2001, *Nature* 412: 283, 285-6) and in polychain formation in vivo (Pickart, 2000, *Trends Biochem. Sci.* 25: 544-8; Mastrandrea, et al., 1999, *J. Biol. Chem.* 274: 27299-306; Spence, et al., 1995, *Mol. Cell. Biol.* 15: 1265-73; Babinoshin and Haas, 1996, *J. Biol. Chem.* 271: 2823-31). Ubiquitination at the $K^{29}$ and $K^{33}$ sites was not observed.

The 98 ubiquitination sites identified were randomly distributed throughout the entire sequence of polypeptides detected with no apparent consensus sequence. For one polypeptide (ECM21p), five sites of ubiquitination were detected, all in the middle third of the polypeptide. However, homologous lysine residues within polypeptide families were found to be modified by ubiquitination (see, FIGS. 10A-C). For example, the sites detected for SNC1p and SNC2p (K62) and HXT6p and HXT7p (K560) were identical.

Examining the 70 polypeptides for the presence of other types of modifications revealed 29 phosphorylation sites from 26 phosphopeptides derived from 19 polypeptides (see, e.g., FIG. 10C). For example, in addition to the 5 ubiquitination sites found for ECM21p, 5 phosphorylation sites were found.

Among the phosphorylated polypeptides detected was ubiquitin itself. A phorphorylated serine residue was identified at $S^{57}$. This serine was recently found to be nonessential for viability in an alanine scanning mutation experiment. However, the crystalline structure of tetraubiquitin suggests this residue is solvent and could potentially interfere with proteosome recognition. Using the methods described above, the presence of phosphorylated species of ubiquitin can be examined in diseased and healthy cells to assess the biological relevance of this modification. Additional ubiquitin-like targets also can be studied, including, but not limited to: Rub1/Nedd8, SUMO, and Apg12 (see, e.g., Hochstrasser, 2000, *Science* 289: 563-564).

Variations, modifications, and other implementations of what is described herein will occur to those of ordinary skill in the art without departing from the spirit and scope of the invention as described and claimed herein and such variations, modifications, and implementations are encompassed within the scope of the invention.

All of the references, patents and patent applications identified hereinabove are expressly incorporated herein by reference.

What is claimed is:

1. A method for determining a relative abundance of ubiquitination in a plurality of ubiquitinated polypeptides in biological samples, the method comprising:
   contacting cellular polypeptides of samples from each of a first cell and a second cell with a binding partner that binds to at least one molecule selected from the group consisting of: a ubiquitin molecule and a molecule linked to ubiquitin, thereby forming ubiquitinated polypeptide:binding partner complexes;
   isolating and separating the ubiquitinated polypeptide:binding partner complexes in the samples from the first cell and the second cell;
   digesting the ubiquitinated polypeptides of the complexes with trypsin, thereby generating a plurality of test peptides;
   determining the presence of at least one isopeptide bond between ubiquitin and an internal lysine residue of at least one of the plurality of test peptides by mass spectrometry by observing at least one mass change of 114 Daltons corresponding to a Gly-Gly residue linked to the internal lysine, wherein the presence of the bond indicates a site or sites of ubiquitination, thereby identifying the ubiquitination site or sites in the first cell and in the second cell; and,
   analyzing the abundance of ubiquitination in the first cell and the second cell by comparing numbers of the ubiquitination site or sites in each of the first cell and in the second cell.

2. The method according to claim 1, further comprising ionizing the plurality of test peptides.

3. The method according to claim 2, further comprising fragmenting the plurality of ionized test peptides.

4. The method according to claim 2, wherein ionizing is performed by an electrospray.

5. The method according to claim 1, further comprising mapping a sequence of at least one in the plurality of test peptides comprising a site of ubiquitination to a polypeptide sequence comprising the same amino acid sequence as in at least one in the plurality of test peptides.

6. The method according to claim 1, wherein separating is performed by at least one round of liquid chromatography.

7. The method according to claim 6, wherein chromatography is performed by reversed-phase liquid chromatography or by high performance liquid chromatography.

8. The method according to claim 1, further comprising detecting multiple ubiquitination sites in a single polypeptide that is ubiquitinated at multiple sites.

9. The method according to claim 1, wherein the binding partner specifically binds to a tag molecule linked to ubiquitin.

10. The method according to claim 9, wherein the ubiquitin molecule comprises histidine-tagged ubiquitin.

11. The method according to claim 9, wherein the ubiquitinated polypeptides are obtained from the first cell and the first cell expresses a tagged ubiquitin molecule.

12. The method according to claim 11, wherein the first cell is a mammalian cell.

13. The method according to claim 11, wherein the first cell is a mouse cell.

14. The method according to claim 1, wherein the first cell is a normal cell and the second cell is from a patient with a pathological condition.

15. The method according to claim 14, wherein the pathological condition is a neurodegenerative disease.

16. The method according to claim 1, wherein the second cell differs from the first cell in expressing a recombinant DNA molecule.

17. The method according to claim 1, further comprising contacting the first cell with a compound and comparing ubiquitination sites identified in the first cell with ubiquitination sites in a second cell not contacted with the compound.

18. The method according to claim 1, further comprising generating a database comprising data files storing information relating to ubiquitination sites for a plurality of polypeptides for a plurality of different cells.

19. The method according to claim 1, wherein the abundance of site or sites of ubiquitination is correlated with disease and wherein detection of ubiquitination at the site or sites is associated with risk of the disease.

20. The method according to claim 1, further comprising the step of determining the presence, site, or amount of a protein modification other than ubiquitination.

* * * * *

SEQUENCE LISTING

<160> NUMBER OF SEQ ID NOS: 59

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His tag

<400> SEQUENCE: 1

His His His His His His
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Ala Leu Lys
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Glu Leu Phe Arg
  1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Phe Thr Gly His Pro Glu Thr Leu Glu Lys
  1               5                  10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Arg Asn Pro Asp
  1               5

<210> SEQ ID NO 6
<211> LENGTH: 10
<212> TYPE: PRT
<213> ORGANISM: Artificial Sequence
<220> FEATURE:

```
<223> OTHER INFORMATION: Description of Artificial Sequence: Synthetic
      His tag
<220> FEATURE:
<221> NAME/KEY: misc_feature
<222> LOCATION: (1)..(10)
<223> OTHER INFORMATION: This region may encompass 6-10 residues

<400> SEQUENCE: 6

His His His His His His His His His His
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Exemplary
      sequence of a signature peptide produced by
      trypsin proteolysis

<400> SEQUENCE: 7

Leu Ile Phe Ala Gly Lys Gln Leu Glu Asp Gly Arg
1               5                   10

<210> SEQ ID NO 8
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 8

Met Pro Phe Ile Thr Ser Arg Pro Val Ala Lys Asn Ser Ser His Ser
1               5                   10                  15

Leu Ser Glu Thr Asp Leu Asn Gln Ser Lys Gly Gln Pro Phe Gln Pro
            20                  25                  30

Ser Pro Thr Lys Lys Leu Gly Ser Met Gln Gln Arg Arg Arg Ser Ser
        35                  40                  45

Thr Ile Arg His Ala Leu Ser Ser Leu Leu Gly Gly
    50                  55                  60

<210> SEQ ID NO 9
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 9

Ala Asn Val His Ser Pro Ala Val Leu Asn Asn Thr Thr Lys Gly Gly
1               5                   10                  15

Asn Asn Asn Gly Asn Ile Arg Ser Ser Asn Thr Asp Ala Gln Leu Leu
            20                  25                  30

Gly Lys Lys Gln Asn Lys Gln Pro Pro Asn Ala Arg Arg His Ser
        35                  40                  45

Thr Thr Ala Ile Gln Gly Ser Ile Ser Asp Ser Ala
    50                  55                  60

<210> SEQ ID NO 10
<211> LENGTH: 60
<212> TYPE: PRT
<213> ORGANISM: Artificial Sequence
<220> FEATURE:
<223> OTHER INFORMATION: Description of Artificial Sequence: Synthetic
```

-continued poly-ubiquitinated polypeptide

<400> SEQUENCE: 10

Thr Thr Thr Pro Arg Ser Ser Thr Asp Thr Asn Arg Arg Thr Ser
1               5                   10                  15

Gly Arg Leu Ser Val Asp Gln Glu Pro Arg Ile Ser Gly Gly Arg Tyr
            20                  25                  30

Ser Gln Ile Glu Glu Asp Ser Thr Val Leu Asp Phe Asp Asp Asp His
        35                  40                  45

Asn Ser Ser Ala Val Val Ser Ser Asp Leu Ser Ser
    50                  55                  60

<210> SEQ ID NO 11
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 11

Thr Ser Leu Thr Arg Leu Ala Asn Ser Lys Lys Phe Asn Glu Gln Phe
1               5                   10                  15

Leu Ile Glu Tyr Leu Thr Ala Arg Gly Leu Leu Gly Pro Lys Thr Val
            20                  25                  30

Leu Ser Asn Glu Tyr Leu Lys Ile Ser Ile Ser Thr Ser Gly Glu Ser
        35                  40                  45

Val Phe Leu Pro Thr Ile Ser Ser Asn Asp Asp Glu
    50                  55                  60

<210> SEQ ID NO 12
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 12

Tyr Leu Ser Arg Leu Asn Gly Leu Asn Asp Gly Thr Asp Asp Ala Glu
1               5                   10                  15

Ala Asp Phe Phe Met Asp Gly Ile Asp Gln Gln Glu Gly Asn Thr Pro
            20                  25                  30

Ser Leu Ala Thr Thr Ala Ala Ala Thr Glu Ser Gly Gly Ser Ile Asn
        35                  40                  45

Glu Asn Arg Asp Thr Leu Leu Arg Glu Asn Asn Ser
    50                  55                  60

<210> SEQ ID NO 13
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 13

Gly Asp His Pro Gly Ser Gly Ser Glu Leu Asn Thr Arg Ser Val Glu
1               5                   10                  15

Ile Asp Ser Ser Met Val Ser Tyr Ser Ile Ala Val Ile Val Ser Val
            20                  25                  30

Lys Lys Pro Thr Arg Phe Thr Asp Met Gln Leu Glu Leu Cys Ser Arg

```
                35                  40                  45

Val Lys Val Phe Trp Asn Thr Gly Val Pro Pro Thr
        50                  55                  60

<210> SEQ ID NO 14
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 14

Lys Thr Phe Asn Glu Glu Phe Tyr Asn Ala Ala Ser Met Lys Trp Asn
1               5                   10                  15

Leu Asn Asp Glu Asn Phe Asp Leu Phe Val Pro Leu Ser Ile Ser Pro
            20                  25                  30

Asp Ile Asp Gln Met Glu Asn Asn Ser Asn Asp Arg Gln Met Arg Leu
        35                  40                  45

Phe Lys Asn Ile Pro Thr Glu Glu Arg Leu Tyr Leu
    50                  55                  60

<210> SEQ ID NO 15
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 15

Asp Lys Thr Lys Thr Lys Ala Ser Leu Leu Asn Ala Ile Asp Val Asn
1               5                   10                  15

Lys Thr His Leu Tyr Gln Pro Gly Asp Tyr Val Phe Leu Val Pro Val
            20                  25                  30

Val Phe Ser Asn His Ile Pro Glu Thr Ile Tyr Leu Pro Ser Ala Arg
        35                  40                  45

Val Ser Tyr Arg Leu Arg Leu Ala Thr Lys Ala Ile
    50                  55                  60

<210> SEQ ID NO 16
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 16

Asn Arg Lys Gly Phe Tyr Arg Gln Asp Ser Asn Ser Pro Gln Pro Ile
1               5                   10                  15

Val Ser Pro Asp Ser Ser Ser Leu Ser Ser Thr Ser Ser Leu
            20                  25                  30

Lys Leu Thr Glu Thr Glu Ser Ala Gln Ala His Arg Arg Ile Ser Asn
        35                  40                  45

Thr Leu Phe Ser Lys Val Lys Asn His Leu His Met
    50                  55                  60

<210> SEQ ID NO 17
<211> LENGTH: 60
<212> TYPE: PRT
<213> ORGANISM: Artificial Sequence
<220> FEATURE:
```

-continued

<223> OTHER INFORMATION: Description of Artificial Sequence: Synthetic
      poly-ubiquitinated polypeptide

<400> SEQUENCE: 17

Ser Ser His Gln Leu Lys Asn Glu Glu Ser Gly Glu Glu Asp Ile Phe
1               5                   10                  15

Ala Glu Tyr Pro Ile Lys Val Ile Arg Thr Pro Pro Val Ala Val
            20                  25                  30

Ser Thr Ala Asn Lys Pro Ile Tyr Ile Asn Arg Val Trp Thr Asp Ser
        35                  40                  45

Leu Ser Tyr Glu Ile Ser Phe Ala Gln Lys Tyr Val
    50                  55                  60

<210> SEQ ID NO 18
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 18

Ser Leu Asn Ser Glu Val Pro Ile Lys Ile Lys Leu Ala Pro Ile Cys
1               5                   10                  15

Lys Asn Val Cys Val Lys Arg Ile His Val Ser Ile Thr Glu Arg Val
            20                  25                  30

Thr Phe Val Ser Lys Gly Tyr Glu Tyr Glu Tyr Asp Gln Thr Asp Pro
        35                  40                  45

Val Ala Lys Asp Pro Tyr Asn Pro Tyr Tyr Leu Asp
    50                  55                  60

<210> SEQ ID NO 19
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 19

Phe Ala Ser Lys Arg Arg Lys Glu Arg Ser Val Ser Leu Phe Glu Ile
1               5                   10                  15

Arg Thr Lys Glu Lys Gly Thr Arg Ala Leu Arg Glu Glu Ile Val Glu
            20                  25                  30

Asn Ser Phe Asn Asp Asn Leu Leu Ser Tyr Ser Pro Phe Asp Asp Asp
        35                  40                  45

Ser Asp Ser Lys Gly Asn Pro Lys Glu Arg Leu Gly
    50                  55                  60

<210> SEQ ID NO 20
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 20

Ile Thr Glu Pro Ile Ile Ile Glu Thr Lys Leu Lys Phe Pro Lys Tyr
1               5                   10                  15

Glu Asp Leu Asp Lys Arg Thr Ala Lys Ile Ile Pro Pro Tyr Gly Ile
            20                  25                  30

Asp Ala Tyr Thr Ser Ile Pro Asn Pro Glu His Ala Val Ala Asn Gly
        35                  40                  45

Pro Ser His Arg Arg Pro Ser Val Ile Gly Phe Leu
        50                  55                  60

<210> SEQ ID NO 21
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 21

Ser Gly His Lys Gly Ser Lys Ser His Glu Glu Asn Glu Lys Pro Val
1               5                   10                  15

Tyr Asp Pro Lys Phe His Gln Thr Ile Ile Lys Ser Asn Ser Gly Leu
                20                  25                  30

Pro Val Lys Thr His Thr Arg Leu Asn Thr Pro Lys Arg Gly Leu Tyr
        35                  40                  45

Leu Asp Ser Leu His Phe Ser Asn Val Tyr Cys Arg
        50                  55                  60

<210> SEQ ID NO 22
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 22

His Lys Leu Glu Ile Met Leu Arg Ile Ser Lys Pro Asp Pro Glu Cys
1               5                   10                  15

Pro Ser Lys Leu Arg His Tyr Glu Val Leu Ile Asp Thr Pro Ile Phe
                20                  25                  30

Leu Val Ser Glu Gln Cys Asn Ser Gly Asn Met Glu Leu Pro Thr Tyr
        35                  40                  45

Asp Met Ala Thr Met Glu Gly Lys Gly Asn Gln Val
        50                  55                  60

<210> SEQ ID NO 23
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 23

Pro Leu Ser Met Asn Ser Asp Phe Phe Gly Asn Thr Cys Pro Pro Pro
1               5                   10                  15

Pro Thr Phe Glu Glu Ala Ile Ser Val Pro Ala Ser Pro Ile Val Ser
                20                  25                  30

Pro Met Gly Ser Pro Asn Ile Met Ala Ser Tyr Asp Pro Asp Leu Leu
        35                  40                  45

Ser Ile Gln Gln Leu Asn Leu Ser Arg Thr Thr Ser
        50                  55                  60

<210> SEQ ID NO 24
<211> LENGTH: 60
<212> TYPE: PRT
<213> ORGANISM: Artificial Sequence

```
<220> FEATURE:
<223> OTHER INFORMATION: Description of Artificial Sequence: Synthetic
      poly-ubiquitinated polypeptide

<400> SEQUENCE: 24

Val Ser Gly Pro Ser Gly Tyr Ser Asp Asp Ala Gly Val Pro Asn Val
1               5                   10                  15

Asn Arg Asn Ser Ile Ser Asn Ala Asn Ala Met Asn Gly Ser Ile Ser
            20                  25                  30

Asn Ser Ala Phe Val Ser Gly Asn Ser Gly Gln Gly Val Ala Arg Ala
        35                  40                  45

Arg Ala Thr Ser Val Asn Asp Arg Ser Arg Phe Asn
    50                  55                  60

<210> SEQ ID NO 25
<211> LENGTH: 60
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 25

Asn Leu Asp Lys Leu Leu Ser Thr Pro Ser Pro Val Asn Arg Ser His
1               5                   10                  15

Asn Ser Ser Pro Thr Asn Gly Leu Ser Gln Ala Asn Gly Thr Val Arg
            20                  25                  30

Ile Pro Asn Ala Thr Thr Glu Asn Ser Lys Asp Lys Gln Asn Glu Phe
        35                  40                  45

Phe Lys Lys Gly Tyr Thr Leu Ala Asn Val Lys Asp
    50                  55                  60

<210> SEQ ID NO 26
<211> LENGTH: 37
<212> TYPE: PRT
<213> ORGANISM: Artificial Sequence
<220> FEATURE:
<223> OTHER INFORMATION: Description of Artificial Sequence: Synthetic
      poly-ubiquitinated polypeptide

<400> SEQUENCE: 26

Asp Glu Glu Gln Glu Gly Ile Val Ser Ser Ser Ala Asp Ser Leu
1               5                   10                  15

Leu Ser His Gly Asn Glu Pro Pro Arg Tyr Asp Glu Ile Val Pro Leu
            20                  25                  30

Met Ser Asp Glu Glu
        35

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      signature peptide

<400> SEQUENCE: 27

Leu Ile Phe Ala Gly Lys Gln Leu Glu Asp Gly Arg
1               5                   10

<210> SEQ ID NO 28
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      signature peptide

<400> SEQUENCE: 28

Thr Leu Ser Asp Tyr Asn Ile Gln Lys Glu Ser Thr Leu His Leu Val
 1               5                  10                  15

Leu Arg

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      signature peptide

<400> SEQUENCE: 29

Thr Leu Thr Gly Lys Thr Ile Thr Leu Glu Val Glu Ser Ser Asp Thr
 1               5                  10                  15

Ile Asp Asn Val Lys
            20

<210> SEQ ID NO 30
<211> LENGTH: 18
<212> TYPE: PRT
<213> ORGANISM: Artificial Sequence
<220> FEATURE:
<223> OTHER INFORMATION: Description of Artificial Sequence: Synthetic
      signature peptide

<400> SEQUENCE: 30

Thr Ile Thr Leu Glu Val Glu Ser Ser Asp Thr Ile Asp Asn Val Lys
 1               5                  10                  15

Ser Lys

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      signature peptide

<400> SEQUENCE: 31

Leu Ile Ser Glu Glu Asp Leu Gly Met Gln Ile Phe Val Lys Thr Leu
 1               5                  10                  15

Thr Gly Lys

<210> SEQ ID NO 32
<211> LENGTH: 19
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 32

Ala Val Ser Val Ser Asp Leu Ser Tyr Val Ala Asn Ser Gln Ser Ser
 1               5                  10                  15

Pro Leu Arg

<210> SEQ ID NO 33
<211> LENGTH: 18
<212> TYPE: PRT
```

```
<213> ORGANISM: Artificial Sequence
<220> FEATURE:
<223> OTHER INFORMATION: Description of Artificial Sequence: Synthetic
      phosphopeptide sequence

<400> SEQUENCE: 33

Gly Ser Gly Gly Thr Ser Glu Leu Gly Gly Ser Glu Ser Thr Pro Leu
  1               5                  10                  15

Leu Arg

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 34

Asp Glu Asn Asp Gly Tyr Ala Ser Asp Glu Val Gly Gly Thr Leu Ser
  1               5                  10                  15

Arg

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 35

Asp Asp Glu Tyr Asp Asp Leu Asn Thr Ile Asp Lys
  1               5                  10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 36

Asn Pro Ser Thr Leu Leu Pro Thr Ser Ser Met Phe Trp Asn Lys
  1               5                  10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 37

Asn Glu Glu Ser Gly Glu Glu Asp Ile Phe Ala Glu Tyr Pro Ile Lys
  1               5                  10                  15

<210> SEQ ID NO 38
<211> LENGTH: 23
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 38
```

```
His Ala Leu Ser Ser Leu Leu Gly Gly Ala Asn Val His Ser Pro Ala
1               5                   10                  15

Val Leu Asn Asn Thr Thr Lys
            20

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 39

Arg Pro Ser Val Ile Gly Phe Leu Ser Gly His Lys
1               5                   10

<210> SEQ ID NO 40
<211> LENGTH: 18
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 40

Ser His Asn Ser Ser Pro Thr Asn Gly Leu Ser Gln Ala Asn Gly Thr
1               5                   10                  15

Val Arg

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 41

Glu Glu Ile Asp Ser Glu Phe Glu Asp Glu Asp Phe Glu Lys
1               5                   10

<210> SEQ ID NO 42
<211> LENGTH: 22
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 42

Ala Ser Gly Glu Thr Ala Ile His Glu Pro Glu Pro Glu Ala Glu Gln
1               5                   10                  15

Ala Val Glu Asp Thr Ala
            20

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 43

Leu Gln Val Val Ser His Glu Thr Asp Ile Asn Glu Asp Glu Glu Glu
```

```
Ala His Tyr Glu Asp Lys
            20

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 44

Lys Tyr Ser Asp Asn Glu Asp Asp Glu Tyr Asp Asp Ala Asp Leu His
1               5                   10                  15

Gly Phe Glu Lys
            20

<210> SEQ ID NO 45
<211> LENGTH: 18
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 45

Arg Gly Ser Val Tyr His Val Pro Leu Asn Pro Val Gln Ala Thr Ala
1               5                   10                  15

Val Arg

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 46

Ile His Asp Thr Ser Asp Glu Asp Met Ala Ile Asn Gly Leu Glu Arg
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 47

Asn Asn Asp Ile Glu Ser Ser Ser Pro Ser Gln Leu Gln His Glu Ala
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 48

Ser Val Asn Tyr Asn Glu Leu Ser Asp Asp Thr Ala Val Lys
1               5                   10                  15
```

```
<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 49

Thr Leu Ser Asp Tyr Asn Ile Gln Lys
 1               5

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 50

Ile Glu Glu Ile Asn Glu Asn Ser Pro Leu Leu Ser Ala Pro Ser Lys
 1               5                  10                  15

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 51

Thr Asn Ser Phe Asp Met Pro Gln Leu Asn Thr Arg
 1               5                  10

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 52

Glu Thr Val Asp Asp Asp Ser Glu Thr Leu Asn Gln Leu Gln Asp Arg
 1               5                  10                  15

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 53

Leu Pro Ser Tyr Glu Glu Ala Ala Gly Thr Pro Lys
 1               5                  10

<210> SEQ ID NO 54
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 54

Lys Asn Pro Asp Glu Asp Glu Phe Leu Ile Asn Ser Asp Asp Glu Met
 1               5                  10                  15

<210> SEQ ID NO 55
<211> LENGTH: 29
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 55

Ser Ser Gly Ile Asp Glu Asp Glu Val Val Thr Pro Ala Glu Asp Ala
 1               5                  10                  15

Lys Glu Glu Glu Glu Glu His Pro Pro Leu Pro Ala Arg
                20                  25

<210> SEQ ID NO 56
<211> LENGTH: 19
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 56

Glu Gln His His Glu Asp Ser Glu Glu Glu Asp Ser Trp Ser Gln Phe
 1               5                  10                  15

Val Glu Lys

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 57

His Val Ile Ala Asp Leu Glu Asp His Glu Ser Ser Asp Glu Glu Gly
 1               5                  10                  15

Thr Ala Leu Pro Lys
                20

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      phosphopeptide sequence

<400> SEQUENCE: 58

Leu Ser Phe Val Phe Gly Gly Thr Asp Glu Lys
 1               5                  10

<210> SEQ ID NO 59
<211> LENGTH: 12
<212> TYPE: PRT
<213> ORGANISM: Artificial Sequence
```

-continued

```
<220> FEATURE:
<223> OTHER INFORMATION: Description of Artificial Sequence: Synthetic
      phosphopeptide sequence

<400> SEQUENCE: 59

Arg Leu Ser Phe Val Phe Gly Gly Thr Asp Glu Lys
  1               5                  10
```